(12) United States Patent
Madabhushi et al.

(10) Patent No.: US 11,350,901 B2
(45) Date of Patent: Jun. 7, 2022

(54) RECURRENCE PROGNOSIS AND PREDICTION OF ADDED BENEFIT OF ADJUVANT CHEMOTHERAPY IN EARLY STAGE NON-SMALL CELL LUNG CANCER WITH RADIOMIC FEATURES ON BASELINE COMPUTED TOMOGRAPHY

(71) Applicant: Case Western Reserve University, Cleveland, OH (US)

(72) Inventors: Anant Madabhushi, Shaker Heights, OH (US); Pranjal Vaidya, Cleveland, OH (US); Vamsidhar Velcheti, Pepper Pike, OH (US); Kaustav Bera, Cleveland, OH (US)

(73) Assignees: Case Western Reserve University, Cleveland, OH (US); The Cleveland Clinic Foundation, Cleveland, OH (US)

(*) Notice: Subject to any disclaimer, the term of this patent is extended or adjusted under 35 U.S.C. 154(b) by 768 days.

(21) Appl. No.: 16/200,710

(22) Filed: Nov. 27, 2018

(65) Prior Publication Data

US 2019/0159745 A1    May 30, 2019

Related U.S. Application Data

(60) Provisional application No. 62/687,417, filed on Jun. 20, 2018, provisional application No. 62/590,920, filed on Nov. 27, 2017.

(51) Int. Cl.
*A61B 6/00* (2006.01)
*G06T 7/00* (2017.01)
(Continued)

(52) U.S. Cl.
CPC ........... *A61B 6/5217* (2013.01); *A61B 6/032* (2013.01); *A61B 6/463* (2013.01); *A61B 6/50* (2013.01);
(Continued)

(58) Field of Classification Search
CPC . G06T 7/0012; G06T 7/12; G06T 7/11; G06T 7/187; G06T 7/136;
(Continued)

(56) References Cited

U.S. PATENT DOCUMENTS

| | | | |
|---|---|---|---|
| 2015/0356730 A1* | 12/2015 | Grove | G06T 7/64 382/124 |
| 2017/0039737 A1* | 2/2017 | Madabhushi | A61B 5/08 |
| 2017/0193657 A1* | 7/2017 | Madabhushi | G06K 9/3233 |

OTHER PUBLICATIONS

Braman, N. M., M. Etesami, P. Prasanna, C. Dubchuk, H. Gilmore, P. Tiwari, D. Plecha, and A. Madabhushi. "Intratumoral and peritumoral radiomics for the pretreatment prediction of pathological complete response to neoadjuvant chemotherapy based on breast DCE-MRI." Breast Cancer Research 19, No. 1 (Year: 2017).*

(Continued)

*Primary Examiner* — Carolyn A Pehlke
(74) *Attorney, Agent, or Firm* — Eschweiler & Potashnik, LLC

(57) ABSTRACT

Embodiments generate an early stage NSCLC recurrence prognosis, and predict added benefit of adjuvant chemotherapy. Embodiments include processors configured to access a radiological image of a region of tissue demonstrating early stage NSCLC; segment a tumor represented in the radiological image; define a peritumoral region based on a morphological dilation of a boundary of the tumor; extract a radiomic signature that includes a set of tumoral radiomic features extracted from the tumoral region, and a set of peritumoral radiomic features extracted from the peritumoral region, based on a continuous time to event data;

(Continued)

compute a radiomic score based on the radiomic signature; compute a probability of added benefit of adjuvant chemotherapy based on the radiomic score; and generate an NSCLC recurrence prognosis based on the radiomic score. Embodiments may display the radiomic score, or generate a personalized treatment plan based on the radiomic score.

20 Claims, 15 Drawing Sheets

(51) Int. Cl.
    *A61B 6/03*     (2006.01)
    *G06T 7/11*     (2017.01)
    *G06T 7/12*     (2017.01)
    *G06V 10/40*     (2022.01)
    *G06V 10/44*     (2022.01)
    *G06V 20/69*     (2022.01)
    *A61B 6/12*     (2006.01)
    *G06T 7/187*     (2017.01)
    *G06T 7/136*     (2017.01)

(52) U.S. Cl.
    CPC ............. *G06T 7/0012* (2013.01); *G06T 7/11* (2017.01); *G06T 7/12* (2017.01); *G06V 10/40* (2022.01); *G06V 10/446* (2022.01); *G06V 20/695* (2022.01); *G06V 20/698* (2022.01); *A61B 6/12* (2013.01); *G06T 7/136* (2017.01); *G06T 7/187* (2017.01); *G06T 2207/10081* (2013.01); *G06T 2207/20076* (2013.01); *G06T 2207/20081* (2013.01); *G06T 2207/20152* (2013.01); *G06T 2207/30061* (2013.01); *G06T 2207/30096* (2013.01); *G06V 2201/031* (2022.01)

(58) Field of Classification Search
    CPC . G06T 2207/30096; G06T 2207/30061; G06T 2207/20152; G06T 2207/20081; G06T 2207/20076; G06T 2207/10081; A61B 6/032; A61B 6/463; A61B 6/50; A61B 6/12; G06K 9/0014; G06K 9/00147; G06K 9/46; G06K 9/4614; G06K 2209/051
    See application file for complete search history.

(56) References Cited

OTHER PUBLICATIONS

Wu, Guoqing, Yinsheng Chen, Yuanyuan Wang, Jinhua Yu, Xiaofei Lv, Xue Ju, Zhifeng Shi, Liang Chen, and Zhongping Chen. "Sparse representation-based radiomics for the diagnosis of brain tumors." IEEE transactions on medical imaging 37, No. 4 (2017): 893-905.*

Rakshit, S, M Orooji, N Beig, M Alilou, N A. Pennell, James Stevenson, Marc A. Shapiro, Anant Madabhushi, and Vamsidhar Velcheti. "Evaluation of radiomic features on baseline CT scan to predict clinical benefit for pemetrexed based chemotherapy in metastatic lung adenocarcinoma." (2016): 11582-11582.*

Prasanna, Prateek, Pallavi Tiwari, and Anant Madabhushi. "Co-occurrence of local anisotropic gradient orientations (CoLlAGe): a new radiomics descriptor." Scientific reports 6, No. 1 (2016): 1-14.*

* cited by examiner

RECURRENCE PROGNOSIS AND PREDICTION OF ADDED BENEFIT OF ADJUVANT CHEMOTHERAPY IN EARLY STAGE NON-SMALL CELL LUNG CANCER WITH RADIOMIC FEATURES ON BASELINE COMPUTED TOMOGRAPHY

CROSS REFERENCE TO RELATED APPLICATIONS

This application claims the benefit of U.S. Provisional Application 62/590,920 filed Nov. 27, 2017, and U.S. Provisional Application 62/687,417, filed Jun. 20, 2018, which are incorporated herein in their entirety.

FEDERAL FUNDING NOTICE

This invention was made with government support under grants CA179327, CA195152, DK098503, CA199374, CA202752, CA208236, RR012463, and CA216579 awarded by the National Institutes of Health; and grants W81XWH-13-1-0418 and W81XWH-14-1-0323, and W81XWH-16-1-0329 awarded by the Department of Defense. The government has certain rights in the invention.

BACKGROUND

Lung cancer may be divided into small cell lung cancer and non-small cell lung cancer (NSCLC). NSCLC accounts for almost 85% of all lung cancer cases. Early-stage non-small cell lung cancer (ES-NSCLC) includes stages IA to IIB disease. ES-NSCLC accounts for approximately 40% of NSCLC cases, with 5-year survival rates varying between 31% and 49%.

Adjuvant cytotoxic chemotherapy (adjuvant chemotherapy) has shown benefits in resected ES-NSCLC patients. Adjuvant chemotherapy is recommended for stage II and stage III disease after surgery with curative intent, and all ES-NSCLC patients are eligible for adjuvant chemotherapy. However, there is a lack of biomarkers which can accurately stratify and predict disease risk in NSCLC. For example, there are no validated radiographic biomarkers to identify patients who would have an additive benefit from adjuvant chemotherapy after surgery. A predictive biomarker provides information about the effect of a therapeutic intervention, and may identify a response to therapy. Thus, the decision to offer adjuvant chemotherapy for NSCLC patients is primarily dependent on several clinical and visual radiographic factors, since there is not an effective existing predictive radiographic biomarker. The existing, clinical or visual radiographic factor-based techniques for predicting added benefit of adjuvant chemotherapy in ES-NSCLC suffer from inter-reviewer inaccuracy, as well as intra-reviewer inaccuracy, and are less than optimal. Indeed, a sizable proportion of NSCLC patients who do not receive adjuvant chemotherapy based on clinical parameters have recurrence.

Surgery is the only potentially curative modality for ES-NSCLC patients. However, 30% to 55% of NSCLC patients develop recurrence. Existing approaches for NSCLC recurrence prognosis suffer from inter-reviewer inaccuracy, as well as intra-reviewer inaccuracy. A prognostic biomarker provides information about the patient's likely overall cancer outcome, regardless or independent of therapy. Thus, an improved approach to NSCLC recurrence prognosis and to predicting added benefit of adjuvant chemotherapy would be advantageous in planning treatment for NSCLC patients. There is an unmet need for a prognostic and predictive biomarker for ES-NSCLC patients to guide therapeutic decision making, and for estimation of patient outcomes regarding treatment modalities.

BRIEF DESCRIPTION OF THE DRAWINGS

The accompanying drawings, which are incorporated in and constitute a part of the specification, illustrate various example operations, apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
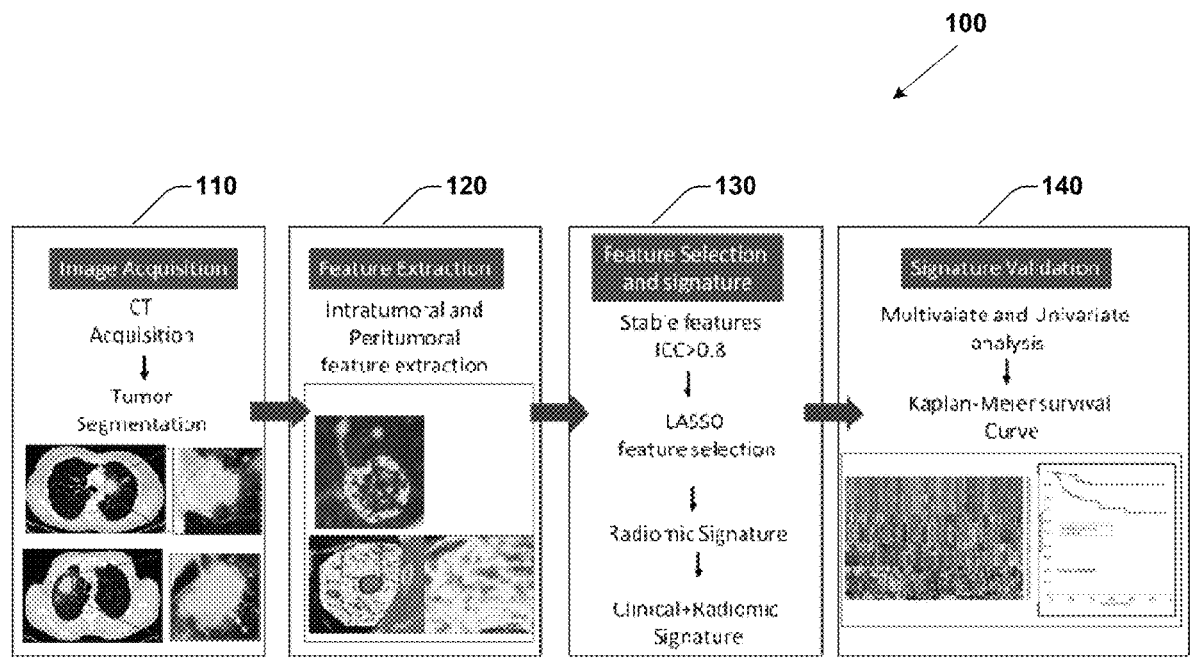
FIG. 1 is a workflow diagram of radiomic analysis for early stage NSCLC recurrence prognosis and added benefit of adjuvant chemotherapy prediction.

Surgery is the only potentially curative modality for early-stage NSCLC. Complete surgical resection is the existing gold standard treatment for early stage NSCLC patients. However, approximately 35% to 55% of early-stage NSCLC patients experience recurrence and have poor prognosis despite curative resection.

Currently, the decision to offer chemotherapy is primarily based on clinical and visual radiographic factors, because there is a lack of a biomarker that can accurately stratify and predict disease risk in early stage NSCLC patients. There is not an established test or biomarker to aid an oncologist or other practitioner in identifying which early stage NSCLC patient will receive added benefit from adjuvant chemotherapy. Furthermore, existing clinical and visual radiographic factors may be susceptible to inter-reviewer variability, or intra-reviewer variability, and are thus suboptimal. Existing treatment guidelines for early stage NSCLC patients suggest the use of adjuvant chemotherapy only for pathologic stage II disease, usually with resected tumor size of greater than 4 cm. However, some patients with smaller sized tumors may also benefit from adjuvant therapy, but are not selected under existing guidelines, and thus fail to realize any benefit from adjuvant therapy. Thus, an improved prognostic biomarker for early stage NSCLC recurrence would be advantageous for improved, more accurate recurrence prognosis, and for improved, more appropriately tailored adjuvant therapy planning based on improved prediction of added benefit of adjuvant chemotherapy.

Embodiments include apparatus, circuits, methods, operations, systems and other embodiments that employ a radiomic signature that includes intra-tumoral and peri-tumoral features extracted from radiological imagery of tissue demonstrating early stage NSCLC, where the radiomic signature is prognostic of disease free survival (DFS) or recurrence, and that is predictive of added benefit of post-surgery adjuvant chemotherapy in early stage NSCLC patients. Embodiments are prognostic of DFS or disease recurrence, and are predictive of added benefit of adjuvant chemotherapy, using a radiomic feature-based model that employs peritumoral and intratumoral radiomic features extracted from a radiological image of a region of tissue demonstrating early stage NSCLC. Embodiments select features based on a continuous data (i.e., time to event (DFS)), and compute a concordance index (CI) for the model, which takes into account the time to event as well as censored information in the dataset used to generate the model.

The CI quantifies the quality of rankings, and is used as a performance measure for model assessment in survival analysis, in this case, DFS or recurrence. The CI indicates the probability of concordance between predicted and observed survival. Embodiments may further combine the radiomic signature with prognostic clinical variables to further facilitate the generation of more accurate DFS prognosis and added benefit prediction. DFS is defined as the time from the date of a patient's CT examination until either the date of relapse (event), which refers to tumor recurrence within or immediately adjacent to the treated field, mediastinal relapse, distant relapse, or death, or until the date that the patient is last known to be free of relapse.

Embodiments may derive a prognostic and predictive model, and define a radiomic signature based on the model, and train a machine learning classifier using the model and the radiomic signature. In one embodiment, five hundred and forty eight (548) ES-NSCLC CT scans from three different institutions were acquired. A first dataset (N=388) of patients from a first institution (CCF) included patients who received surgery after tumor detection and other patients who received chemotherapy following surgery. The first dataset was divided into two cohorts based on the treatment received (e.g., surgery after tumor detection, or chemotherapy following surgery). A first group from the first CCF dataset included the patients who received surgery after tumor detection. A second group from the CCF dataset included the patients who received chemotherapy following surgery. A second dataset from CCF (N=292) in conjunction with the RIDER test-retest dataset (N=31) was used as a discovery cohort. In one embodiment, the discovery cohort is a dedicated learning set of cases not used in the validation of the model. The discovery set in this case enables the identification of the most stable features that are also predictive of disease outcome.

A model employed by embodiments is evaluated using an independent validation cohort (N=144) acquired from a second institution (UPenn). To evaluate a predictive assay of the model, a second dataset from CCF (N=96) was used with patients who received chemotherapy following surgery. In one embodiment described herein, a training dataset may have a minimum follow-up time of twenty-nine (29) days and a maximum follow up time of 3468 days, with median follow-up of 1126 days. A validation dataset may have minimum, maximum, and median follow-up times of twenty-two (22), 758, and 4741 days, respectively. The second group from the CCF dataset that includes patients who received chemotherapy following surgery has minimum, maximum, and median follow-up times of 104, 2798, and nine-hundred and fifty (950) days, respectively.

Embodiments extract radiomic features from tumoral regions and peritumoral regions represented in CT imagery. A CT image (i.e., a scan) may include a plurality of slices. A CT image slice, may have a thickness of from 1 mm to 5 mm. Different CT images may have different slice thicknesses. In one embodiment, lung tumors represented in the CT image are retrospectively contoured on three dimensional (3D) slicer software by an expert radiologist to segment the lesion (i.e., tumor) from non-tumor tissue represented in the CT imagery, and to define a tumor boundary. Automated segmentation techniques may be employed, including a region growing technique, thresholding, or a watershed approach, to segment the tumor and define the tumor boundary.

FIG. 1 is a workflow diagram of radiomic analysis for early stage NSCLC recurrence prognosis and added benefit of adjuvant chemotherapy prediction. FIG. 1 illustrates, at 110, image acquisition and tumor segmentation of an early stage NSCLC tumor represented in a CT image. The tumor region may be segmented manually using a 3D slicer software, or may be segmented automatically. For example, the tumor region may be segmented using a region growing technique, a thresholding approach, or a watershed approach. Segmenting the tumor includes defining a tumoral boundary that defines the tumor region, where the tumor region has a volume. The 3D tumor region is divided into a plurality of two dimensional (2D) sections (i.e., slices). In one embodiment, from the plurality of 2D sections that comprise the 3D volume of the tumor region, the three 2D sections having the largest areas are selected for feature extraction. In another embodiment, different selection criteria may be used to select a 2D section from which to extract features. For example, more than three, or fewer than three, 2D sections may be selected for feature extraction. In another embodiment, the image acquired may be a 2D image. In another embodiment, three slices are selected for extracting 2D features. The slice which has the maximum tumor area is selected as the main slice from which to extract 2D features. In this embodiment, the two slices immediately adjacent to the main slice are also selected. 2D features are extracted from these scans and combined together to calculate statistics of these features for individual patients.

Figure 2:
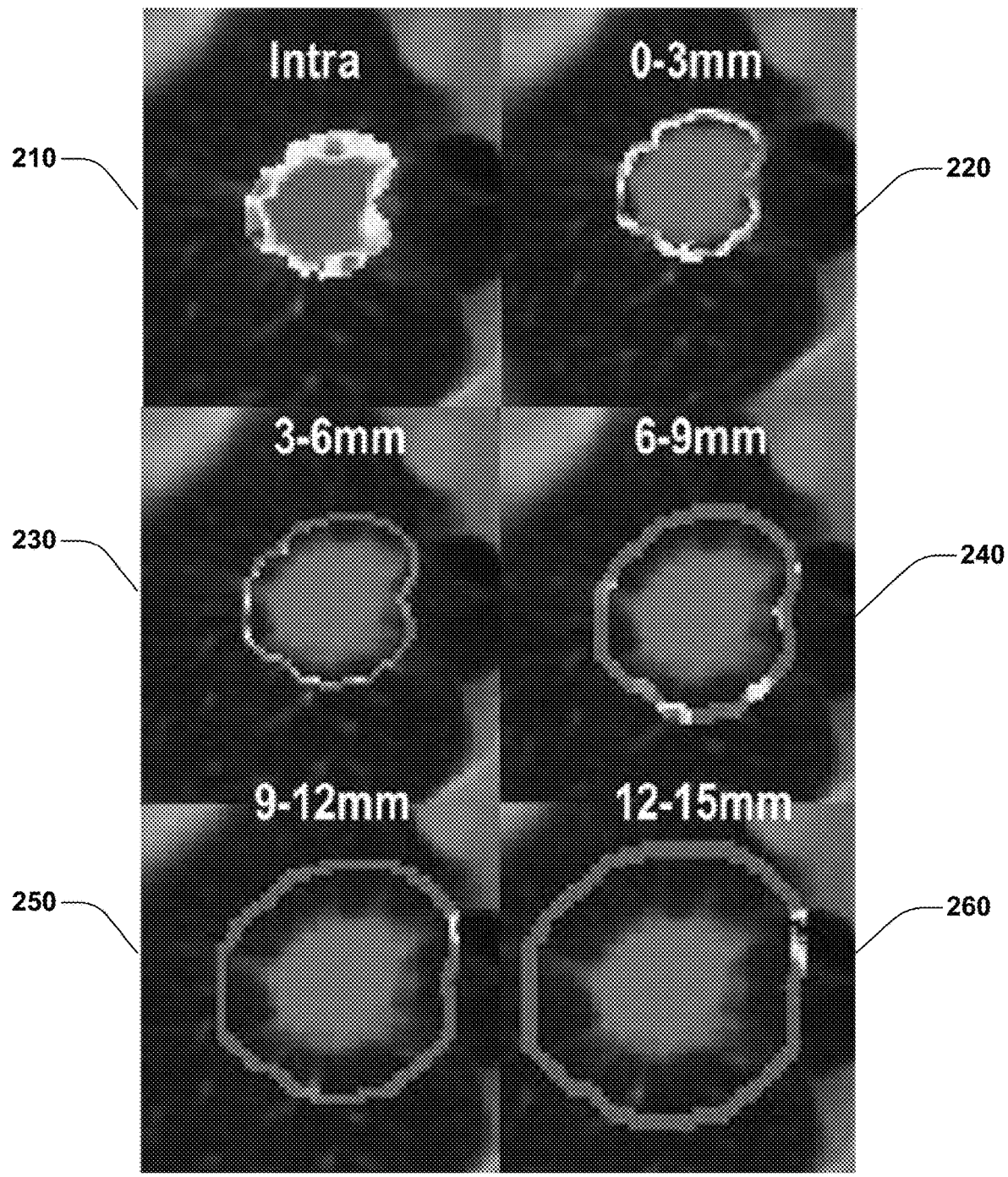
FIG. 2 illustrates an exemplary peritumoral region.
Figure 13:
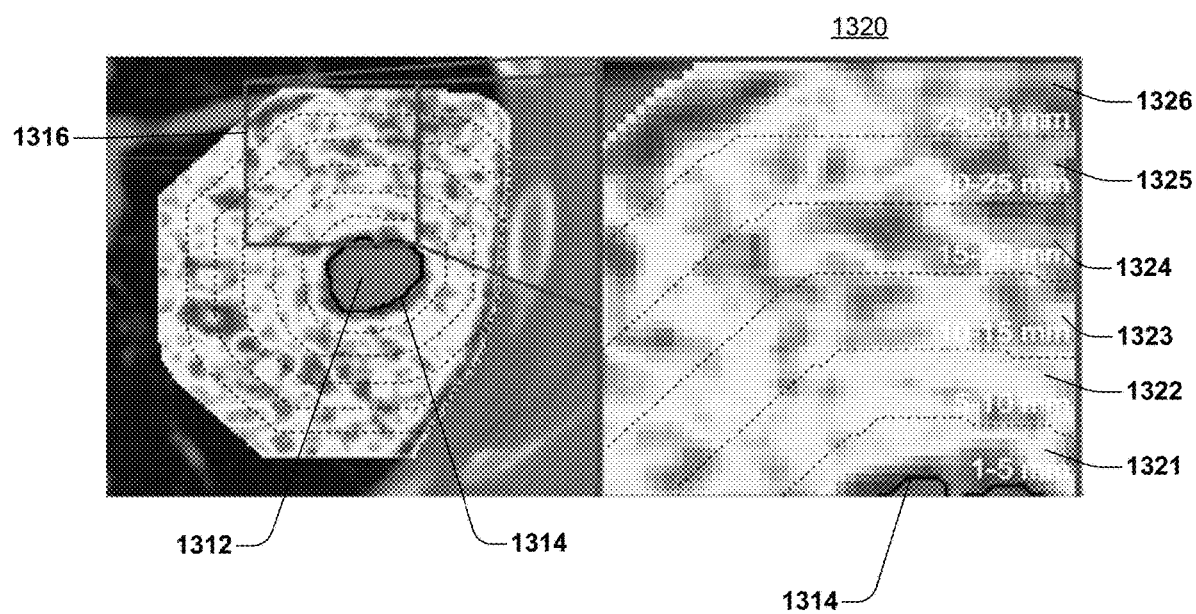
FIG. 13 illustrates an exemplary peritumoral region.

Embodiments define a peritumoral region using quantitative morphological operations on the tumoral boundary. For example, a peritumoral region may be defined as a region extending radially from the tumoral boundary. In one embodiment, the peritumoral region is defined by dilating the tumoral boundary radially 15 mm. In other embodiments, the peritumoral region may be defined by dilating the tumor boundary other distances (e.g., 10 mm, 12 mm). FIG. 2 illustrates an example peritumoral region defined around a tumoral region 210. The peritumoral region includes five annular rings 220-260, having a width of 3 mm respectively. FIG. 13 illustrates another example of peritumoral region 1316 defined around a tumoral region 1312. The tumoral boundary 1314 is dilated 30 mm, and six annular rings 1321-1326 having a width of 5 mm respectively are illustrated at 1320. In other embodiments, other morphological operations may be employed to define the peritumoral region. Embodiments further remove the effect of skin, air, or lipids that may be captured by dilating the tumor boundary. In one embodiment, removing the effect of skin, air, or lipids includes applying kernel-based morphologic closing and opening operations to remove objects that are extraneous to the tumor and not part of the tumor.

Embodiments extract radiomic features from the intratumoral (i.e., tumoral) and peritumoral regions of pre-treatment CT imagery. FIG. 1 illustrates, at 120, intratumoral and peritumoral feature extraction. In this embodiment, thirteen (13) Haralick features, thirteen (13) co-occurrence of local anisotropic gradients (CoLlAGe) features, twenty-five (25) Laws features, twenty-five Laplace features, and forty-eight (48) Gabor features, are extracted from the intratumoral and peritumoral regions. In other embodiments, other numbers of radiomic features, or different radiomic features, may be extracted.

Haralick features capture textural patterns and are predictive of variation in tumor microarchitecture, heterogeneity, and the local appearance of nodules. CoLlAGe features capture textural entropy structural disorder by applying gray level co-occurrence matrix (GLCM) metrics of disorder to local dominant intensity gradients. Laws features and Laplace features are filter-based descriptors that capture textural patterns. Gabor features capture spatial frequencies within the image at directional orientations.

Embodiments compute first-order statistics, including mean, median, skewness, standard deviation (SD), kurtosis, or range of the extracted radiomic features. In one embodiment, first-order statistics are computed for each feature across all pixels of the three slices with the largest tumor area, or of the largest slice and two adjacent slices, for an image. In another embodiment, first-order statistics are computed for less than all the pixels (e.g., 90%, 75%, 50%) for an image, or for other combinations of slices. The percentage of pixels for which first-order statistics are computed may be user selectable, and may be based on, for example, a desired level of prognostic or predictive accuracy, or a desired use of computational resources.

In one embodiment, radiomic features are extracted from annular rings within the peritumoral region. For example, in an embodiment where the peritumoral region is defined by a 15 mm dilation of the tumoral boundary, radiomic features are extracted from five annular rings defined on 3 mm increments from the tumoral boundary. In other embodiments, other numbers of annular rings, or annular ring increments (e.g., 2 mm, 4 mm, 5 mm) may be employed.

FIG. 2 illustrates exemplary radiomic features extracted from an intratumoral region at 210, and from a peritumoral region with annular rings having a 3 mm increment at 220-260. FIG. 13 illustrates a peritumoral region that includes six annular rings of 5 mm width.

Embodiments may evaluate radiomic feature stability and reproducibility, select radiomic features based on the feature stability and reproducibility, and construct a radiomic signature from the selected radiomic features. FIG. 1 illustrates, at 130, feature selection and radiomic signature construction. In one embodiment, feature stability and reproducibility was evaluated using the RIDER test-retest dataset. The RIDER test-retest dataset contains imagery acquired of 31 lung cancer patients, scanned two times within fifteen minutes of each scan. Two scans of every patient in the RIDER dataset were used for calculating an intra class correlation coefficient (ICC). In this embodiment, the cases in the RIDER dataset include individual patients who had been scanned twice on the same scanner within a small time interval (e.g., a first scan at a first time, and a second scan acquired at a second, slightly later, time, for example 15 minutes later). Thus the images and corresponding radiomic features from the two scans for a patient separated within a short interval of each other may ideally be identical, but on account of slight differences in every acquisition, are not. ICC measures similarity between two feature vectors. In one embodiment, using an ICC threshold of 0.7, all feature vectors having an ICC value less than the threshold were removed from analysis. In another embodiment, the ICC threshold may have another, different value (e.g., 0.8, 0.9).

Embodiments may reduce the number of features used to construct a radiomic signature. Reducing the number of features used to construct the radiomic signature improves the performance of NSCLC recurrence prognosis systems, systems that predict added benefit of adjuvant chemotherapy, or computers, processors, or other machines on which embodiments described herein may operate. Improvements include at least the technical effect of reducing the computational complexity of predicting added benefit or of making the NSCLC recurrence prognosis, of reducing the computational complexity required in computing the radiomic score for a patient, or in reducing the number of radiomic features considered for constructing the radiomic signature. Reducing the computational complexity or reducing the number of radiomic features considered may have the technical effect of reducing the energy consumption of, or increasing the speed of, NSCLC recurrence prognosis systems, systems that predict added benefit of adjuvant chemotherapy, or computers, processors, or other machines on which embodiments described herein may operate.

In one embodiment, a least absolute shrinkage and selection operator (LASSO) Cox regression model is employed on the discovery cohort. Depending on the regulation weight lambda, LASSO shrinks all regression coefficients towards zero and set the coefficients of other irrelevant features exactly to zero. Embodiments may employ ten-fold cross validation with minimum criteria to find an optimal lambda, where the final value of lambda yields minimum cross validation error. In one embodiment, the R package glmnet is employed for LASSO Cox regression modeling. Embodiments may determine which radiomic features have non-zero coefficients, and use those features for regression model fitting, combining those features to develop a radiomic signature. A radiomic score for a patient is obtained through linear combination of raw values for extracted features weighted by their LASSO model coefficients. The radiomic scores obtained from patients in the training test are then employed to build a continuous radiomic signature. At least one advantage of a continuous risk score is that unlike existing binary classification approaches, the continuous risk score does not mandate the arbitrary selection of a threshold to determine "favorable" and "unfavorable" prognostic categories. For instance, in an existing approach, a medical practitioner may be required to select an arbitrary threshold of five years to decide on whether a patient who has NSCLC recurrence within or beyond five years had a favorable or unfavorable prognosis. Embodiments that compute a continuous risk score do not require specifying such a threshold, instead providing a discrete number of aggressiveness to each patient. Embodiments may validate the radiomic signature.

FIG. 1 illustrates, at 140, radiomic signature validation. Embodiments may validate the radiomic signature using techniques including multivariate and univariate analysis, and representative Kaplan-Meier survival curves.

Embodiments provide improved performance with respect to disease recurrence prognostic accuracy, and improved prediction of added benefit of adjuvant chemotherapy, compared to existing approaches and existing clinical variables. Existing clinical prognostic factors include tumor size, lymphovascular status (LVI-present, absent), T status (T0, T1, T2), Nodal status (N0, N1, N2), and pathologic stage (i.e., overall stage IA, IB, IIA, and IIB). While these clinical variables have been shown to have prognostic and predictive performance for ES-NSCLC, embodiments offer improved prognostic and predictive performance. For instance within early stage lung cancers (stages I and II), clinical variables are not prognostic of early recurrence or likelihood of added benefit of adjuvant chemotherapy. The radiomic features employed by embodiments are both prognostic and predictive in these early stage tumors.

Embodiments discover a stable set of radiomic features from which to construct a radiomic signature that is prognostic of DFS and that predicts added benefit of adjuvant chemotherapy. In one embodiment, from a set of stable radiomic features, sixteen (16) radiomic features had non-zero coefficients in the LASSO Cox regression models. A rad-score (i.e., radiomic score) is calculated using a linear combination of a raw radiomic feature's value multiplied by its corresponding LASSO coefficient. Based on a continuous value, patients are divided into high-risk of BCR and low-risk of BCR groups. In embodiments described herein, a stable set of radiomic features may be defined using the RIDER test-retest dataset. Radiomic features with ICC>0.7 were considered for further analysis which reduced total number of features from 4386 to 2097. From this feature set, most correlated features were removed using Pearson correlation (correlation factor=0.9) and the LASSO feature selection technique was employed on the remaining 395 features. Ten (10) features had non-zero LASSO coefficient. These 10 features were used for constructing a radiomic signature by linear combination of raw feature values multiplied by corresponding LASSO coefficient, respectively. Using the discovery cohort, the continuous signature was divided into four groups and patients were divided into high-risk and low-risk groups based on the signature score. Patients having radiomic score greater than 75% (fourth quarter of cases) were considered at high risk and those having less than 75% threshold (1 to 3 quarters) were considered low risk patients. These groups were used for Kaplan-Meier analysis.

In one embodiment, the top features selected are used for unsupervised cluster analysis. Corresponding CT scans from 50 patients with corresponding whole slide tissue scans were used for agglomerative clustering. The two clusters revealed from the analysis were compared against clinical factors and TIL density features extracted from the corresponding whole slides. Patients were divided into high-TILs and low-TILs based on the median value of the cohort. There was significant association with recurrence (p<0.005, $\chi 2$ test) and treatment (p<0.05, $\chi 2$ test). The first cohort representing high-risk nodules had 64% high-TILs concentration.

Figure 3:
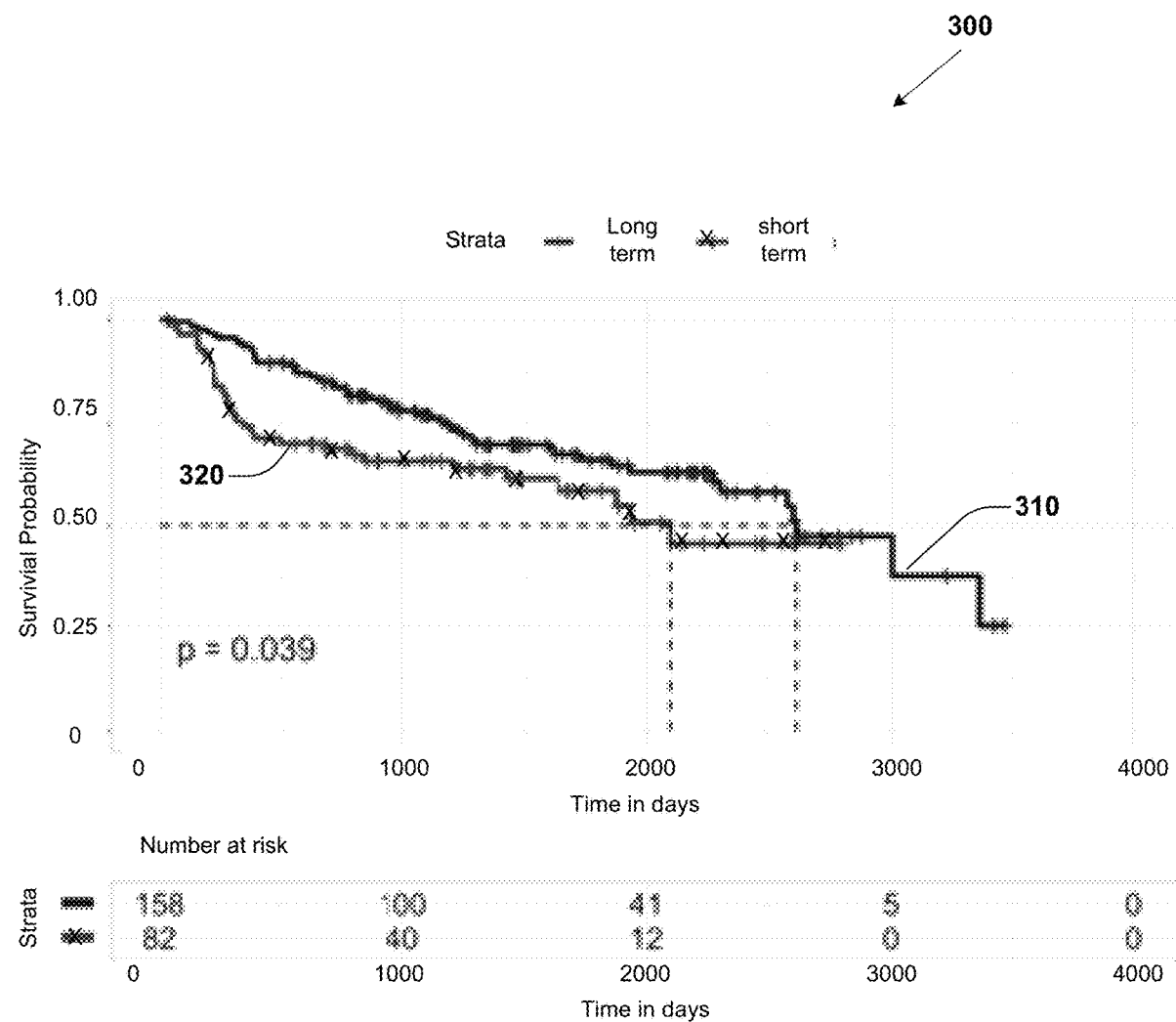
FIG. 3 is a graph illustrating a Kaplan-Meier curve with median threshold for a training cohort.
Figure 4:
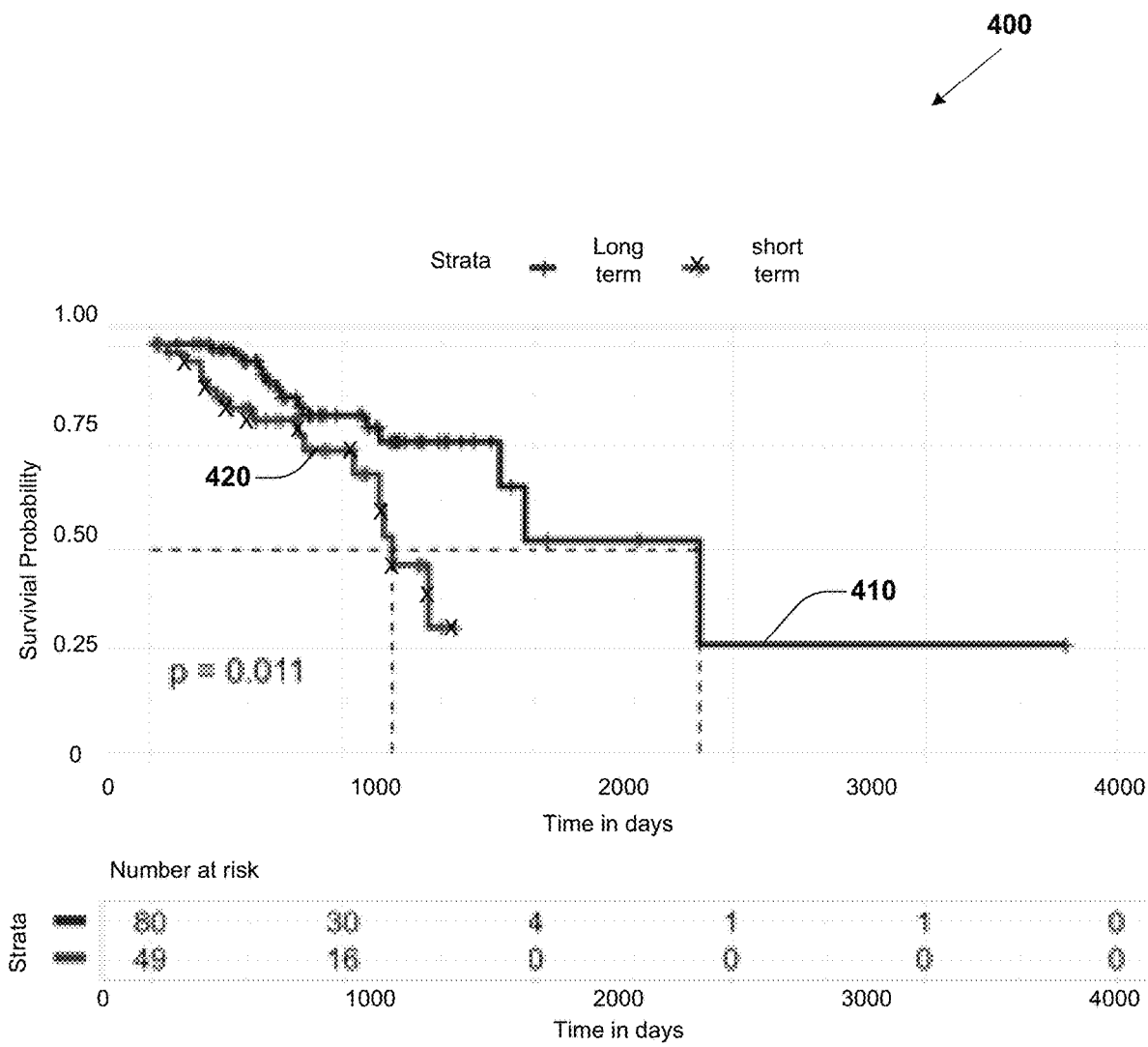
FIG. 4 is a graph illustrating a Kaplan-Meier curve with median threshold for a validation cohort.

Embodiments employing a radiomic signature derived from extracted radiomic features are prognostic of DFS. In one embodiment, a multivariate analysis using a radiomic signature as described herein is prognostic of DFS with a concordance index of 0.61 on a training set and with a concordance index of 0.62 on a validation set. Based on a median threshold from the training cohort, patients are separated into high-risk and low-risk groups. FIGS. 3 and 4 illustrate graphs 300 and 400 of Kaplan-Meier curves that show statistically significant separation between predicted high-survival and low-survival groups for the training cohort (FIG. 3) and the validation cohort (FIG. 4) respectively. Graph 300 includes, at 310, a Kaplan-Meier curve for patients in a training cohort with long-term DFS, while the Kaplan-Meier curve for patients from the same cohort with short-term DFS is illustrated at 320. Graph 400 includes, at 410, a Kaplan-Meier curve for patients in a validation cohort with long-term DFS, while the Kaplan-Meier curve for patients from the same validation cohort with short-term DFS is illustrated at 420. The Kaplan-Meier (KM) curves, as illustrated in FIGS. 3 and 4, indicate that patients with lower Rad-Score have better disease-free survival, whereas high-rad scores indicate aggressive tumor regions. On both training cohort and validation cohorts, predicted high-risk and low-risk groups had statistically significant separation (p<0.005) with KM analysis. In the training cohort, 23 patients out of 73, and 16 out of 41 cases in validation cohort, had confirmed recurrence/death within 3 years' threshold within the high risk group. Whereas, in the low-risk group, only 30 out of 218 and 10 out of 88 had recurrence in training and validation cohorts respectively.

Figure 14:
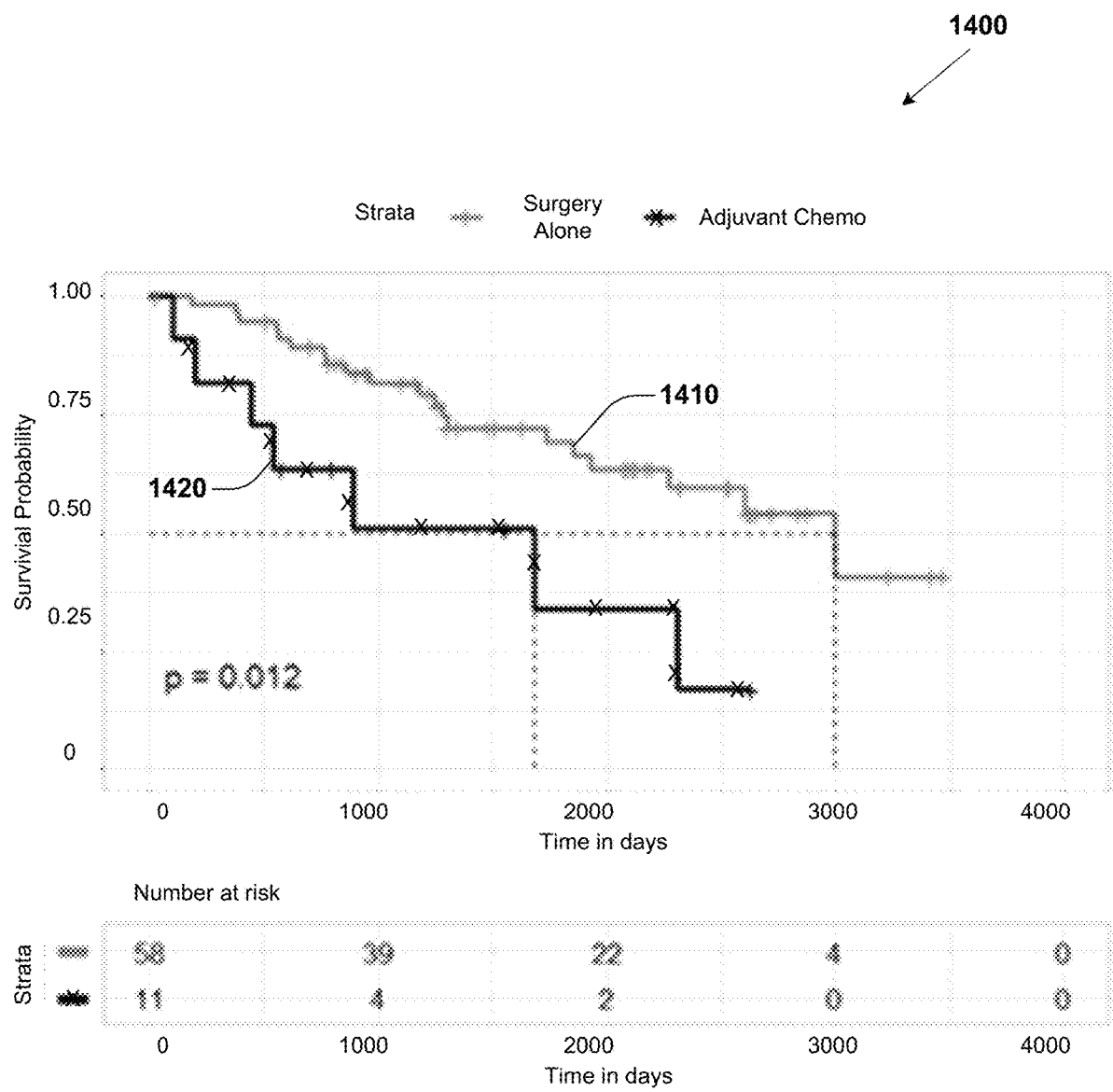
FIG. 14 is a graph illustrating a Kaplan-Meier curve for patients receiving surgery alone and adjuvant chemotherapy having low radiomic scores as computed by embodiments described herein.
Figure 15:
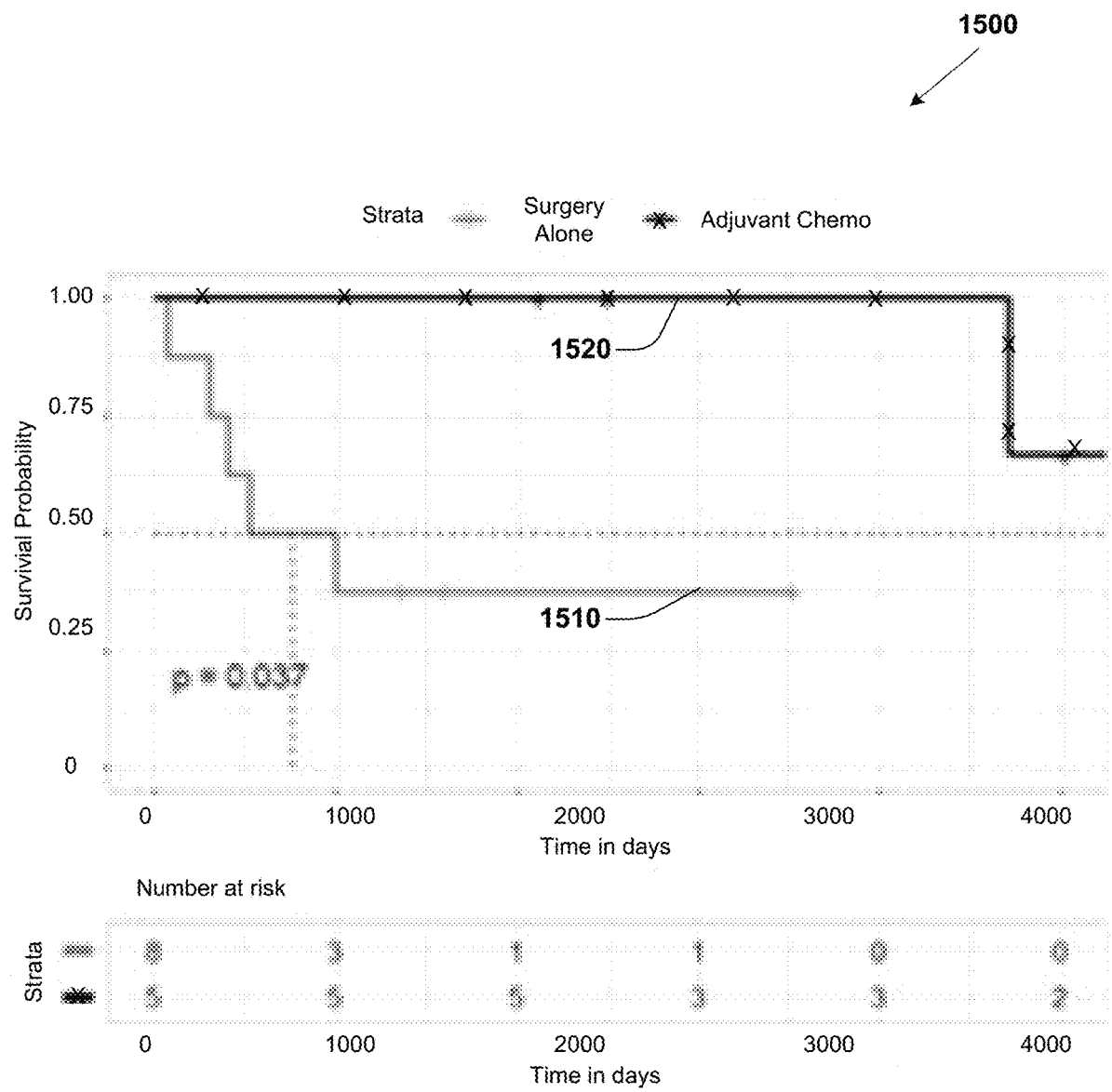
FIG. 15 is a graph illustrating a Kaplan-Meier curve for patients receiving surgery alone and adjuvant chemotherapy having high radiomic scores as computed by embodiments described herein.

Embodiments employing the radiomic signature derived from extracted radiomic features are predictive of added benefit of adjuvant chemotherapy. In one embodiment, the validation cohort was divided into patients who received surgery alone, and patients who received chemotherapy following surgery. The associated radiomic signature was compared against these two cohorts. FIG. 14 illustrates Kaplan-Meier curves 1410 and 1420 for the surgery alone cohort and surgery plus adjuvant chemotherapy cohort respectively, for patients having low radiomic scores. FIG. 15 illustrates Kaplan-Meier curves 1510 and 1520 for the surgery alone cohort and surgery plus adjuvant chemotherapy cohort respectively for patients having a high radiomic score. As illustrated in FIG. 15, the survival curves 1510 and 1520 indicate that patients having high radiomic scores had significantly better DFS in the adjuvant chemotherapy cohort compared to the surgery alone cohort. Similarly, FIG. 14 illustrates that patients with low radiomic scores had no difference between the surgery-adjuvant chemotherapy group and the surgery alone group. Thus, FIGS. 14 and 15 further indicate that embodiments are predictive of added benefit of chemotherapy, and prognostic of recurrence.

Embodiments facilitate improved early stage NSCLC recurrence prognosis, and improved prediction of added benefit of adjuvant chemotherapy compared to existing approaches, including approaches that rely on prognostic clinical variables alone, or that rely on intratumoral radiomic features alone. Embodiments facilitate the development of lower cost predictive companion diagnostic assays for identifying patients who may receive added benefit from adjuvant chemotherapy. Embodiments improve the accuracy of early stage NSCLC recurrence prognosis systems, apparatus, and computers, and further improve the accuracy of systems, apparatus, and computers that predict added benefit of adjuvant chemotherapy.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 5:
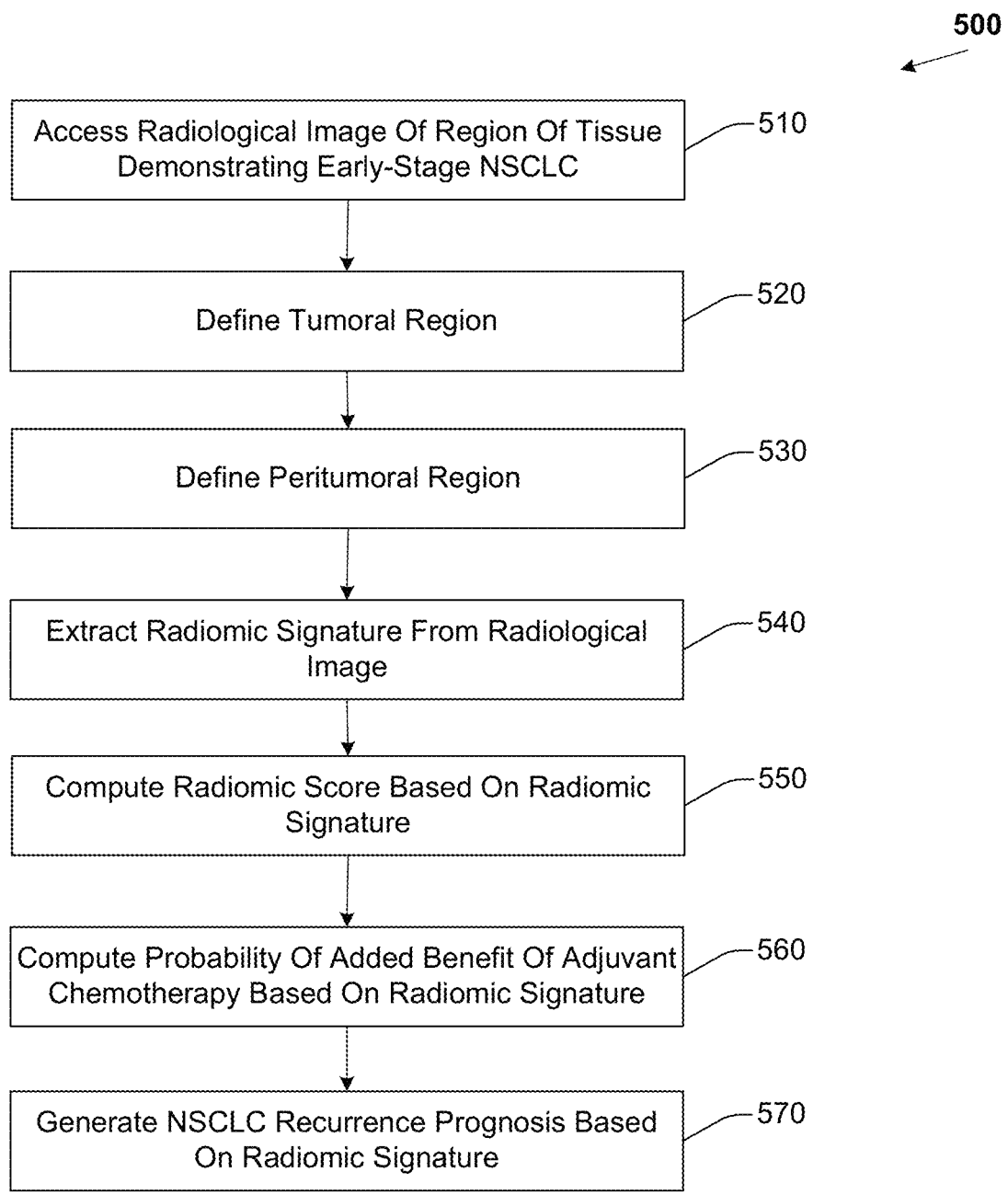
FIG. 5 is a flow diagram of example operations for early stage NSCLC recurrence prognosis and added benefit of adjuvant chemotherapy prediction.

FIG. 5 is a flow diagram of example operations 500 that may be performed by a processor for providing an early stage NSCLC recurrence prognosis, and for predicting added benefit of response to adjuvant chemotherapy in early stage NSCLC. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 500 includes, at 510, accessing a radiological image of a region of tissue demonstrating early stage NSCLC. The region of tissue includes an NSCLC tumor. Accessing the radiological image includes acquiring electronic data, reading from a computer file, receiving a computer file, reading from a computer memory, or other computerized activity. The radiological image has a plurality of pixels, a pixel having an intensity. In one embodiment, the radiological image is a 3D CT image that includes a representation of the tumor. A 3D CT image has a plurality of voxels. The 3D CT image may have a plurality of slices, where a member of the plurality of slices has a thickness of 1 mm to 5 mm. In another embodiment, the radiological image may be acquired using other, different imaging parameters, including different slice thicknesses, different numbers of slices, or different reconstruction kernels. In another embodiment, the radiological image may be a magnetic resonance image (MRI), or a spectral CT image or a PET scan image. The radiological image may be a baseline radiological image acquired before surgery to treat NSCLC, and before the administration of adjuvant chemotherapy to treat NSCLC.

The set of operations 500 also includes, at 520, defining a tumoral region. Embodiments define the tumoral region by segmenting the tumor represented in the radiological image. Defining the tumoral region includes defining a tumoral boundary. In one embodiment, segmenting the tumor represented in the radiological image includes segmenting the tumor using an automated segmentation technique. For example, in one embodiment, the tumor may be segmented using watershed segmentation, region growing segmentation, or thresholding-based segmentation. In another embodiment, other segmentation techniques may be employed. Defining the tumoral region, in this embodiment, includes acquiring electronic data, reading from a computer file, receiving a computer file, reading from a computer memory, or other computerized activity. In one embodiment, the tumoral region may be pre-defined.

In embodiments described herein, the tumor has a volume, and segmenting the tumor includes dividing the volume into a plurality of slices. A slice of the tumor has a boundary. A slice also has an area defined by the boundary. The number of slices in the plurality of slices may be a function of the volume, may be a function of a desired level of computational complexity, or may be user defined. Embodiments may select a member of the plurality of slices from which to extract radiomic features having the largest area. In a situation in which two different slices have the same area, a slice may be selected randomly, may be selected manually, or may be selected base on other criteria, including nearness to the centroid of the tumor.

The set of operations 500 also includes, at 530, defining a peritumoral region based on a morphological dilation of the tumoral boundary. The peritumoral region may include a plurality of annular rings. An annular ring is defined by embodiments by applying a morphological operation (e.g., dilation) to the tumoral boundary. For example, the tumoral boundary may be dilated a first incremental amount to generate a first annular ring. In one embodiment, the peritumoral region includes five annular rings, generated with a dilation increment of 3 mm. Thus, a first annular ring would include a region extending from the boundary outward 3 mm, a second annular ring would include a region extending from the 3 mm dilation to 6 mm, and so on. FIG. 2 illustrates a tumoral region 210. FIG. 2 also illustrates annular rings 220-260 having a 3 mm dilation increment. FIG. 13 illustrates annular rings 1021-1026 of a peritumoral region 1316.

FIG. 13 illustrates a slice of a tumor volume represented in CT imagery. A tumor region 1312 includes a boundary 1314. A peritumoral region 1316 including six annular rings 1321-1326 is defined by dilating the boundary 1314. The six annular rings 1321-1326 are illustrated at a greater magnification at 1320. In this example, the annular rings are dilated from the boundary 1314 by a dilation increment of 5 mm, although in other embodiments, other dilation increments (e.g., 2 mm, 3 mm, 4 mm, 6 mm) may be employed. In another embodiment, the peritumoral region may be defined using other techniques. For example, a set of concentric spheres or circles may be defined around the centroid of the tumor, or a set of concentric ellipsoids may be defined around the centroid of the tumor. In one embodiment, the peritumoral region may be pre-defined.

The set of operations 500 also includes, at 540, extracting a radiomic signature from the radiological image. The radiomic signature includes a set of tumoral radiomic features extracted from the tumoral region, and a set of peritumoral radiomic features extracted from the peritumoral region. The set of tumoral radiomic features and the set of peritumoral radiomic features are selected based on a continuous time to event data. In one embodiment, the continuous time to event data is a disease free survival (DFS) time of a training set of radiological images of a region of tissue demonstrating early stage NSCLC. Extracting the set of tumoral radiomic features or the set of peritumoral radiomic features includes acquiring electronic data, reading from a computer file, receiving a computer file, reading from a computer memory, or other computerized activity.

In one embodiment, the set of tumoral radiomic features includes at least one of a Haralick feature, a co-occurrence of local anisotropy gradients (CoLIAGe) feature, a Laws feature, a Laplace feature, or a Gabor feature. In another embodiment, the set of tumoral radiomic features may include other, different radiomic features.

In one embodiment, the set of peritumoral radiomic features includes at least one of a Haralick feature, a CoLIAGe feature, a Laws feature, a Laplace feature, or a Gabor feature. In another embodiment, the set of peritumoral radiomic features may include other, different radiomic features.

The set of operations 500 also includes, at 550, computing a radiomic score. The radiomic score is computed based on the radiomic signature. In one embodiment, the radiomic score is computed using a linear combination of a raw feature value of a member of the set of tumoral radiomic features or a member of the set of peritumoral radiomic features, multiplied by a least absolute shrinkage and selection operator (LASSO) coefficient of the raw feature value of the member of the set of tumoral radiomic features or the member of the set of peritumoral radiomic features, respectively. The radiomic score may, in one embodiment, exist on a range of [0, 1]. In one embodiment, the training cohort is used for standardizing the radiomic score with a mean of 0 and a standard deviation of 1. The radiomic signature on the validation cohort was standardized based on a training cohort. In this example, the radiomic score has a range between −2 and 3.5. Computing the radiomic score includes acquiring electronic data, reading from a computer file, receiving a computer file, reading from a computer memory, or other computerized activity.

The set of operations 500 also includes, at 560, computing a probability of added benefit of adjuvant chemotherapy. The probability of added benefit of adjuvant chemotherapy is computed based, at least in part, on the radiomic score. Computing the probability of added benefit includes acquiring electronic data, reading from a computer file, receiving a computer file, reading from a computer memory, or other computerized activity.

The set of operations 500 also includes, at 570, generating an NSCLC recurrence prognosis. The NSCLC recurrence prognosis is computed based, at least in part, on the radiomic score. Generating the NSCLC recurrence prognosis includes acquiring electronic data, reading from a computer file, receiving a computer file, reading from a computer memory, or other computerized activity.

In one embodiment, computing the probability of added benefit of adjuvant chemotherapy, and generating the NSCLC recurrence prognosis, includes providing the radiomic score to a machine learning classifier. In one embodiment, the machine learning classifier is configured to discriminate early stage NSCLC tissue that experiences recurrence from early stage NSCLC tissue that does not experience recurrence, and configured to compute a score on a continuous scale that a region of tissue demonstrating early stage NSCLC will experience added benefit of adjuvant chemotherapy. The machine learning classifier computes the score of added benefit of adjuvant chemotherapy, and generates the NSCLC recurrence prognosis, based, at least in part, on the radiomic score. In this embodiment, computing the score further includes receiving from the machine learning classifier, the score.

In embodiments described herein, the prognosis for NSCLC disease free survival is inversely related to the radiomic score, and the probability of added benefit of adjuvant chemotherapy is directly related to the radiomic score. For example, a higher radiomic score indicates worse survival and a higher probability of NSCLC recurrence, while lower radiomic score indicates low probability of recurrence and better disease-free survival. Also, a higher radiomic score indicates a higher likelihood of added benefit of adjuvant chemotherapy, while a lower radiomic score indicates a lower likelihood of added benefit of adjuvant chemotherapy.

Figure 6:
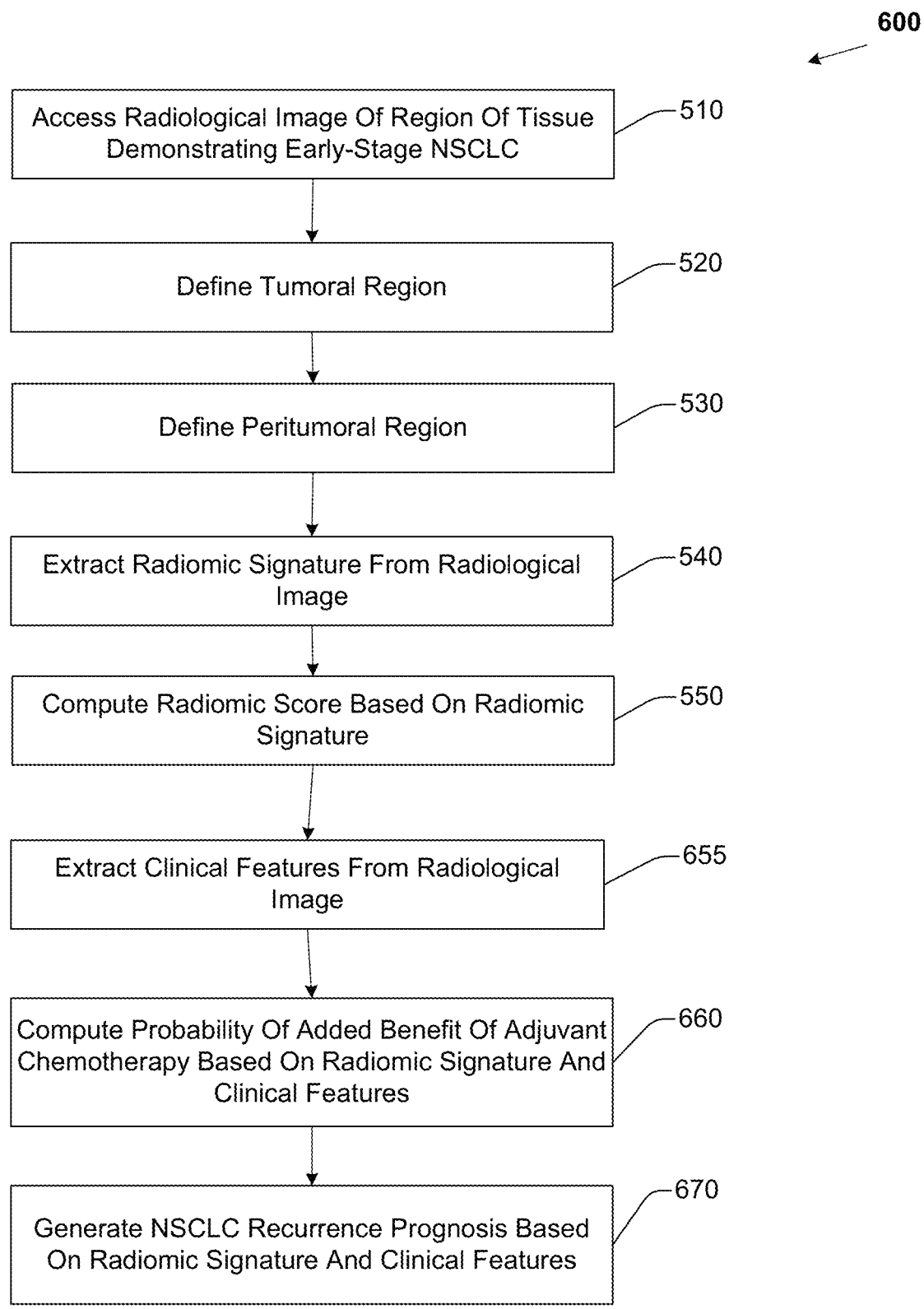
FIG. 6 is a flow diagram of example operations for early stage NSCLC recurrence prognosis and added benefit of adjuvant chemotherapy prediction.

FIG. 6 illustrates a set of operations 600 that is similar to operations 500, but that includes additional elements and details. The set of operations 600 includes, at 655, extracting a set of clinical features from the radiological image. In one embodiment, the set of clinical features includes at least one of a tumor size, a lymphovascular status, a T status, a Nodal status, or a pathologic stage. In another embodiment, the set of clinical features may include other, different clinical features. Extracting the set of clinical features includes acquiring electronic data, reading from a computer file, receiving a computer file, reading from a computer memory, or other computerized activity.

The set of operations 600 also includes, at 660, computing the probability of added benefit of adjuvant chemotherapy. In this embodiment, the probability of added benefit of adjuvant chemotherapy is computed based, at least in part, on the radiomic score and the set of clinical features.

The set of operations 600 also includes, at 670, generating the NSCLC recurrence prognosis. In this embodiment, the NSCLC recurrence prognosis is generated based, at least in part, on the radiomic score and the set of clinical features. Embodiments may generate the NSCLC recurrence prognosis or compute the probability of added benefit using univariate as well as multivariate models. For example, in one embodiment, univariate analysis is performed for individual clinical features as well as the radiomic signature for calculating individual hazard ratios and concordance indexes. The univariate analysis reveals association of these variables with DFS and proves them to be independent predictors of DFS. Next, a combined analysis is performed using the multivariate regression model. For a patient, clinical variables and the radiomic signature are combined in the multivariate model for calculating a combined concordance index. The prognostic performance of the clinical model improves after the addition of radiomic signature. The prognostic clinical features are used for the analysis and compared against the radiomic signature. These clinical features include tumor size, pathologic stage, lymphovascular status (LVI), N stage and T stage. Embodiments that employ a combined model with clinical and radiomic factors as described herein produce a concordance index of 0.73, which is an improvement on existing approaches.

Figure 7:
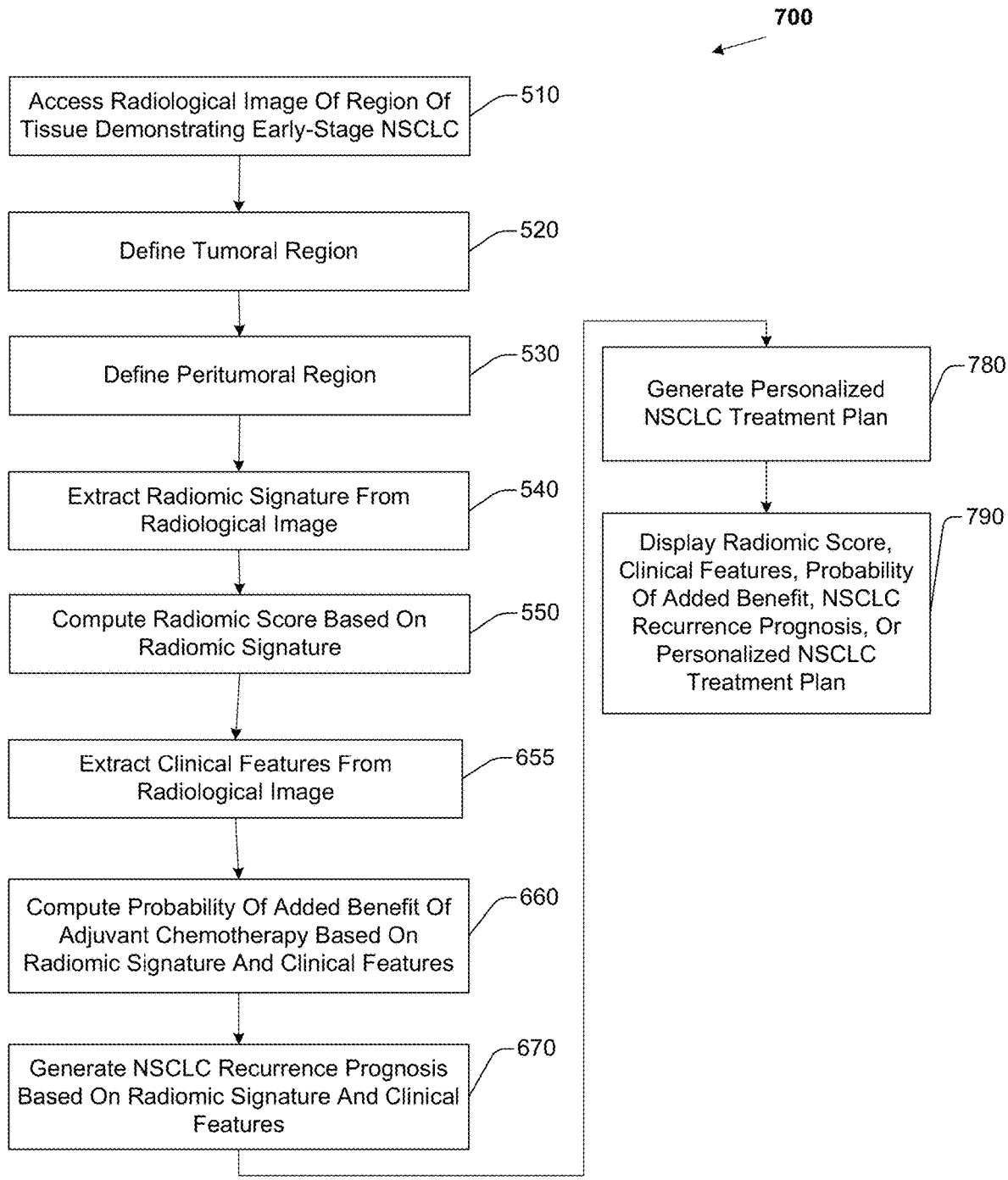
FIG. 7 is a flow diagram of example operations for early stage NSCLC recurrence prognosis and added benefit of adjuvant chemotherapy prediction.

FIG. 7 illustrates a set of operations 700 that is similar to operations 500 and operations 600, but that includes additional steps and details. The set of operations 700 includes, at 780, generating a personalized NSCLC treatment plan. The personalized NSCLC treatment plan is based on at least one of the radiomic score, the probability of added benefit of adjuvant chemotherapy, the NSCLC recurrence prognosis, or a member of the set of clinical features. Generating a personalized treatment plan facilitates the technical effect of delivering a particular treatment that will be therapeutically active to the patient, while minimizing negative or adverse effects experienced by the patient. For example, the personalized treatment plan may suggest a surgical treatment, may define an immunotherapy agent dosage or schedule, or a chemotherapy agent dosage or schedule, the probability of added benefit of adjuvant chemotherapy is high. For a region of tissue where the probability of added benefit of adjuvant chemotherapy is low, other treatments may be suggested. Similarly, the personalized treatment plan may suggest a first treatment for a first NSCLC recurrence prognosis, and suggest a second, different treatment for a second, different NSCLC recurrence prognosis.

The set of operations 700 further includes, at 790, displaying at least one of the radiomic score, a member of the set of clinical features, the probability of added benefit of adjuvant chemotherapy, the NSCLC recurrence prognosis, or the personalized NSCLC treatment plan. Displaying at least one of the radiomic score, a member of the set of clinical features, the probability of added benefit of adjuvant chemotherapy, the NSCLC recurrence prognosis, or the personalized NSCLC treatment plan may include displaying at least one of the radiomic score, a member of the set of clinical features, the probability of added benefit of adjuvant chemotherapy, the NSCLC recurrence prognosis, or the personalized NSCLC treatment plan on a computer monitor, a smartphone display, a tablet display, or other displays. Displaying at least one of the radiomic score, a member of the set of clinical features, the probability of added benefit of adjuvant chemotherapy, the NSCLC recurrence prognosis, or the personalized NSCLC treatment plan may also include printing at least one of the radiomic score, a member of the set of clinical features, the probability of added benefit of adjuvant chemotherapy, the NSCLC recurrence prognosis, or the personalized NSCLC treatment plan. Displaying at least one of the radiomic score, a member of the set of clinical features, the probability of added benefit of adjuvant chemotherapy, the NSCLC recurrence prognosis, or the personalized NSCLC treatment plan may also include controlling a computer assisted diagnosis (CADx) system, a monitor, or other display, to display operating parameters or characteristics of a machine learning classifier, during both training and testing, or during clinical operation of the machine learning classifier. By displaying at least one of the radiomic score, a member of the set of clinical features, the probability of added benefit of adjuvant chemotherapy, the NSCLC recurrence prognosis, or the personalized NSCLC treatment plan, example embodiments provide a timely and intuitive way for a human pathologist to more accurately classify pathologies demonstrated by a patient, thus improving on existing approaches to predicting disease recurrence or predicting added benefit of adjuvant chemotherapy.

Embodiments described herein may also classify the region of tissue as likely to experience recurrence, or unlikely to experience recurrence based, at least in part, on the radiomic score, or the NSCLC recurrence prognosis. The region of tissue may be classified as, for example, "likely to experience recurrence", "unknown", or "unlikely to experience recurrence", or other classification based on the radiomic score, or the NSCLC recurrence prognosis. Embodiments may classify the region of tissue as likely to receive added benefit from adjuvant chemotherapy, or unlikely to receive added benefit, based on the radiomic score, or the probability of added benefit of adjuvant chemotherapy. The region of tissue may also be classified as, for example, "likely to receive added benefit", "unknown", or "unlikely to receive added benefit", or other classification based on the radiomic score, or the probability of added benefit of adjuvant chemotherapy. In another embodiment, the region of tissue may be classified as likely to experience recurrence, or unlikely to experience recurrence based, at least in part, on the radiomic score, and the set of clinical features. In another embodiment, the region of tissue may be classified as likely to receive added benefit, or unlikely to receive added benefit based, at least in part, on the radiomic score, and the set of clinical features.

In embodiments described herein, generating the NSCLC recurrence prognosis, or computing the probability that the region of tissue will receive added benefit from adjuvant chemotherapy, may include providing the radiomic score to a machine learning classifier. In one embodiment, the machine learning classifier is an LDA classifier configured to discriminate early stage NSCLC tissue that experiences recurrence from early stage NSCLC tissue that does not experience recurrence. In this embodiment, generating the NSCLC recurrence prognosis, or computing the probability that the region of tissue will receive added benefit from adjuvant chemotherapy receiving from the machine learning classifier, the NSCLC recurrence prognosis, or the probability that the region of tissue will receive added benefit from adjuvant chemotherapy. In another embodiment, the machine learning classifier may be a quadratic discriminant analysis (QDA) classifier, a support vector machine (SVM) classifier, or may include a convolutional neural network or other deep-learning classifier.

In one embodiment, the operations may further include training the machine learning classifier. In this embodiment, the machine learning classifier is trained and tested using a training set of images and a testing set of images. The training set of images, and the testing set of images, include imagery from patients that experienced long-term DFS, and short-term DFS. The training set and the testing set also include imagery from patients that were subject to surgery alone, and from patients that were subject to adjuvant chemotherapy post-surgery. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed. Training the machine learning classifier may also include determining which tumoral radiomic features and which peritumoral features are most discriminative in distinguishing tissue likely to experience recurrence from tissue unlikely to experience recurrence, or are most discriminative in predicting added benefit of adjuvant chemotherapy. Training the machine learning classifier may further include determining which clinical features, in combination with selected tumoral radiomic features peritumoral features, are most discriminative in distinguishing tissue likely to experience recurrence from tissue unlikely to experience recurrence, or are most discriminative in predicting added benefit of adjuvant chemotherapy.

While FIGS. 5-7 illustrate various actions occurring in serial, it is to be appreciated that various actions illustrated in FIGS. 5-7 could occur substantially in parallel. By way of illustration, a first process could involve accessing a radiological image, a second process could involve extracting tumoral radiomic features, and a third process could involve extracting peritumoral radiomic features from the radiological image. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage device may store computer executable instructions that if executed by a machine (e.g., computer, processor) cause the machine to perform methods or operations described or claimed herein including methods 1100 or 1200, operations 500, 600, or 700, or any other methods or operations described herein. While executable instructions associated with the listed methods are described as being stored on a computer-readable storage device, it is to be appreciated that executable instructions associated with other example methods or operations described or claimed herein may also be stored on a computer-readable storage device. In different embodiments the example methods or operations described herein may be triggered in different ways. In one embodiment, a method or operation may be triggered manually by a user. In another example, a method or operation may be triggered automatically.

Improved NSCLC recurrence prognosis or improved prediction of added benefit of adjuvant chemotherapy may produce the technical effect of improving treatment efficacy by increasing the accuracy of and decreasing the time required to treat patients demonstrating early stage NSCLC, or other forms of cancerous pathology. Treatments and resources, including expensive immunotherapy agents or chemotherapy may be more accurately tailored to patients with a likelihood of benefiting from said treatments and resources, including responding to immunotherapy or chemotherapy, so that more appropriate treatment protocols may be employed, and expensive resources are not wasted. Controlling a personalized medicine system, a CADx system, a processor, an NSCLC recurrence prognosis system, or an added benefit of adjuvant chemotherapy prediction system based on improved, more accurate prognosis, identification, or classification of tissue further improves the operation of the system, processor, or apparatus, at least because the accuracy of the system, processor, or apparatus is increased, and unnecessary operations will not be performed.

Embodiments described herein, including at least methods 1100 or 1200, the sets of operations 500, 600, and 700, apparatus 800 and 900, and computer 1000, resolve features extracted from radiological imagery, including CT imagery, at a higher order or higher level than a human can resolve in the human mind or with pencil and paper. For example, the peritumoral radiomic features of cancerous tissue are not properties of the tissue that a human eye can perceive. A tumor does not include a set of pixels with intensities, two-dimensional slices, a set of annular peritumoral rings, or CoLlAGe features, and these features cannot be stored in a human mind. Embodiments described herein use a combined order of specific rules, elements, operations, or components that render information into a specific format that is then used and applied to create desired technical results more accurately, more consistently, and with greater reliability than existing approaches, thereby producing the technical effect of improving the performance of the machine, computer, or system with which embodiments are implemented.

Using a more appropriately modulated treatment may lead to less aggressive therapeutics being required for a patient or may lead to avoiding or delaying a biopsy, a resection, or other invasive procedure. When patients demonstrating early stage NSCLC who are likely to experience recurrence are more accurately distinguished from patients who are unlikely to experience recurrence, patients most at risk may receive a higher proportion of scarce resources (e.g., therapeutics, physician time and attention, hospital beds) while those less likely to benefit from the treatment, or less in need, may be spared unnecessary treatment, which in turn spares unnecessary expenditures and resource consumption. Similarly, patients who are more likely to experience added benefit of adjuvant chemotherapy may receive a higher proportion of scarce resources (e.g., therapeutics, physician time and attention, hospital beds) while those less likely to benefit from the treatment, or less in need, may be spared unnecessary treatment. Example methods, apparatus, and other embodiments may thus have the additional technical effect of improving patient outcomes and reducing patient suffering compared to existing approaches.

Figure 8:
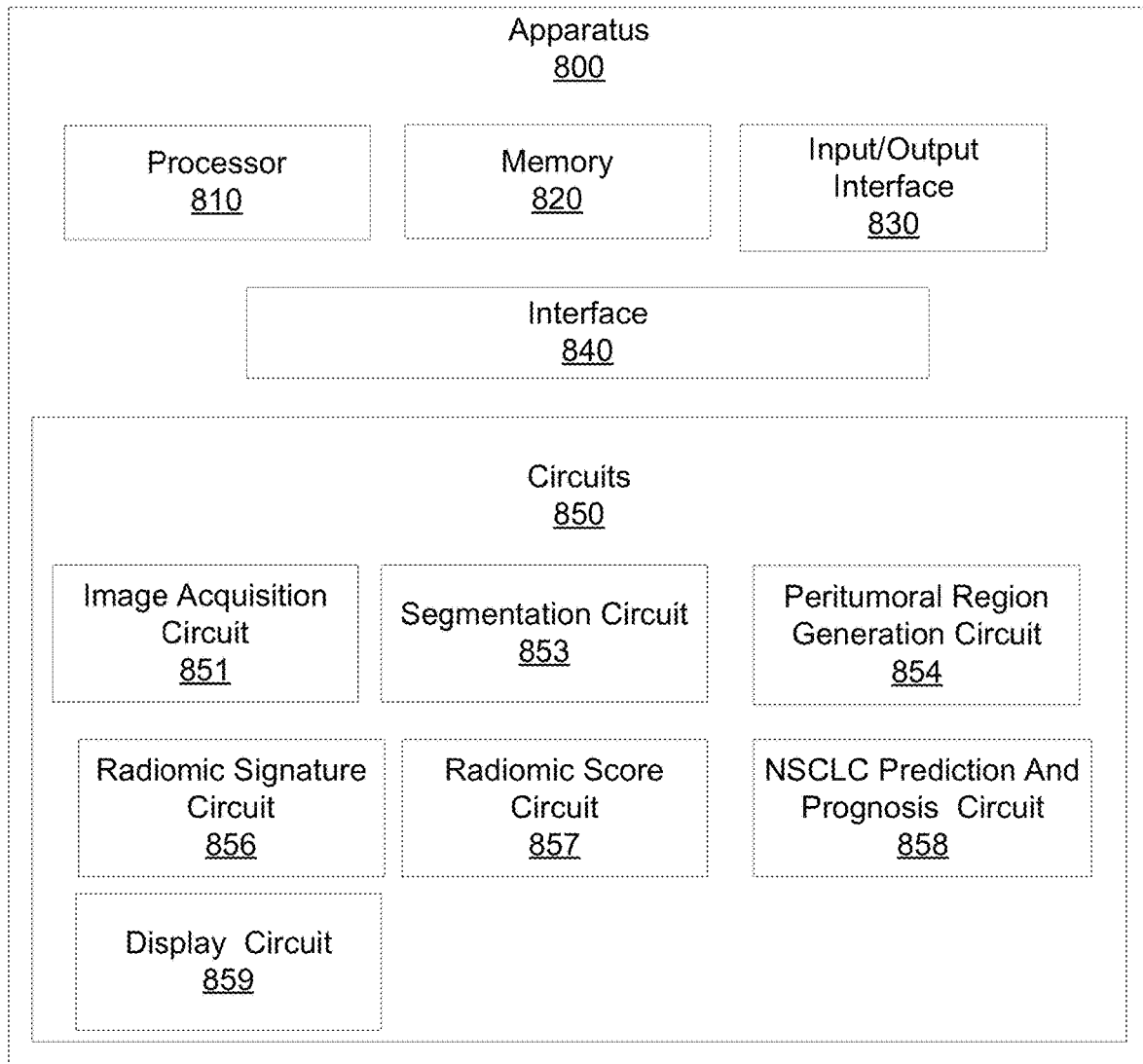
FIG. 8 illustrates an example apparatus for early stage NSCLC recurrence prognosis and added benefit of adjuvant chemotherapy prediction.

FIG. 8 illustrates an example apparatus 800 for early stage NSCLC. recurrence prognosis, and for predicting added benefit of adjuvant chemotherapy in early stage NSCLC. Apparatus 800 includes a processor 810. Apparatus 800 also includes a memory 820. Processor 810 may, in one embodiment, include circuitry such as, but not limited to, one or more single-core or multi-core processors. Processor 810 may include any combination of general-purpose processors and dedicated processors (e.g., graphics processors, application processors, etc.). The processors may be coupled with or may include memory (e.g. memory 820) or storage and may be configured to execute instructions stored in the memory or storage to enable various apparatus, applications, or operating systems to perform the operations. Memory 820 is configured to store a radiological image of a region of tissue demonstrating early stage NSCLC. The radiological image has a plurality of pixels, a pixel having an intensity. In one embodiment, the radiological image is a 3D CT image that includes a representation of a tumor region. Memory 820 may be further configured to store a training set that includes a plurality of radiological images, where a member of the plurality of radiological images includes a region of tissue demonstrating NSCLC, where the region of tissue includes a tumor. Memory 820 may be further configured to store a testing set that includes a plurality of radiological images, where a member of the plurality of radiological images includes a region of tissue demonstrating NSCLC, where the region of tissue includes a tumor.

Apparatus 800 also includes an input/output (I/O) interface 830, a set of circuits 850, and an interface 840 that connects the processor 810, the memory 820, the I/O interface 830, and the set of circuits 850. I/O interface 830 may be configured to transfer data between memory 820, processor 810, circuits 850, and external devices, for example, a CADx system or a personalized medicine system.

The set of circuits 850 includes an image acquisition circuit 851, a segmentation circuit 853, a peritumoral region generation circuit 854, a radiomic signature circuit 856, a radiomic score circuit 857, an NSCLC prediction and prognosis circuit 858, and a display circuit 859.

Image acquisition circuit 851 is configured to access a radiological image of a region of tissue demonstrating early stage NSCLC. The region of tissue represented in the radiological image includes a tumor. The radiological image may be a three-dimensional (3D) computed tomography (CT) image. In another embodiment, other types of radiological image, including MRI images, may be accessed. Accessing the radiological image may include accessing the radiological image stored in memory 820. In one embodiment, accessing the radiological image may including accessing a radiological image stored in a data storage device, including a hard disk drive, a solid state device, a tape drive, accessing a radiological image over a local area network, or from the cloud. Accessing the radiological image includes acquiring electronic data, reading from a computer file, receiving a computer file, reading from a computer memory, or other computerized activity.

Segmentation circuit 853 is configured to define a tumoral region by segmenting the tumor represented in the radiological image. Segmenting the tumor region includes defining a tumoral boundary. In one embodiment, segmentation circuit 853 is configured to segment the tumor using a watershed segmentation technique. In another embodiment, segmentation circuit 853 may be configured to employ other segmentation techniques, including thresholding, edge-based techniques, or region growing. In another embodiment, the tumoral boundary may have already been defined. In one embodiment, the tumoral region is defined in three dimensions.

Segmentation circuit 853 may be further configured to divide the tumor represented in the radiological image into a plurality of tumor slices. For example, a tumor represented in a 3D CT image has a volume defined by a boundary, and the volume may be divided into slices. A slice of the volume (e.g., a tumor slice) has a boundary. The tumor slice has an area defined by the boundary. A tumor slice may be a 2D slice. The number of tumor slices may be a function of the volume of the tumor, may be based on a desired level of computational resource usage, or may be manually selected. Segmentation circuit 853 may be further configured to select a member of the plurality of tumor slices having the largest area. In one embodiment, if more than one member of the plurality of slices having the largest area have the same area, segmentation circuit 853 is configured to randomly select a member of the more than one member of the plurality of slices having the largest area.

Peritumoral region generation circuit 854 is configured to define a peritumoral region. Peritumoral region generation circuit 854 defines the peritumoral region based on a morphological dilation of the tumoral boundary. The peritumoral region may include a plurality of annular rings. An annular ring is defined by embodiments by applying a morphological operation (e.g., dilation) to the tumoral boundary. For example, the tumoral boundary may be dilated a first incremental amount to generate a first annular ring. In one embodiment, the peritumoral region includes five annular rings, generated with a dilation increment of 3 mm. Thus, a first annular ring would include a region extending from the boundary outward 3 mm, a second annular ring would include a region extending from the 3 mm dilation to 6 mm, and so on. In another embodiment, peritumoral region generation circuit 854 is configured to define the peritumoral region using other, different morphological operations. In one embodiment, the peritumoral region may have already been defined.

Radiomic signature circuit 856 is configured to extract a radiomic signature from the radiological image. The radiomic signature includes a set of tumoral radiomic features extracted from the tumoral region. The radiomic signature also includes a set of peritumoral radiomic features extracted from the peritumoral region. The set of tumoral radiomic features and the set of peritumoral radiomic features are selected based on a continuous time to event data. The continuous time to event data may be disease free survival time.

In one embodiment, the set of tumoral radiomic features includes at least one of a Haralick feature, a CoLlAGe feature, a Laws feature, a Laplace feature, or a Gabor feature. In this embodiment, the set of peritumoral radiomic features includes at least one of a Haralick feature, a CoLlAGe feature, a Laws feature, a Laplace feature, or a Gabor feature. In another embodiment, the set of tumoral radiomic features or the set of peritumoral radiomic features may include other, different radiomic features.

Radiomic score circuit 857 is configured to compute a radiomic score based on the radiomic signature. In one embodiment, radiomic score circuit 857 is configured to compute the radiomic score using a linear combination of a raw feature value of a member of the set of tumoral radiomic features or a member of the set of peritumoral radiomic features, multiplied by a LASSO coefficient of the raw feature value of the member of the set of tumoral radiomic features or the member of the set of peritumoral radiomic features respectively.

NSCLC prediction and prognosis circuit 858 is configured to compute a probability of added benefit of adjuvant chemotherapy based, at least in part, on the radiomic score. NSCLC prediction and prognosis circuit 858 is further configured to generate an NSCLC recurrence prognosis based, at least in part, on the radiomic score. The NSCLC recurrence prognosis is inversely related to the radiomic score. The probability of added benefit of adjuvant chemotherapy is directly related to the radiomic score. Embodiments are configured to compute the probability of added benefit, and the NSCLC recurrence prognosis, based on the radiomic score, with a concordance index of at least 0.65.

Display circuit 859 is configured to display the radiomic score. In one embodiment, display circuit 859 is further configured to display at least one of the NSCLC recurrence prognosis, the probability of added benefit, or the radiological image. Display circuit 859 is configured to display the radiomic score and at least one of the NSCLC recurrence prognosis, the probability of added benefit, or the radiological image on a computer monitor, a smartphone display, a tablet display, or other displays. Displaying at least one of the NSCLC recurrence prognosis, the probability of added benefit, or the radiological image may also include printing at least one of the NSCLC recurrence prognosis, the probability of added benefit, or the radiological image.

Figure 9:
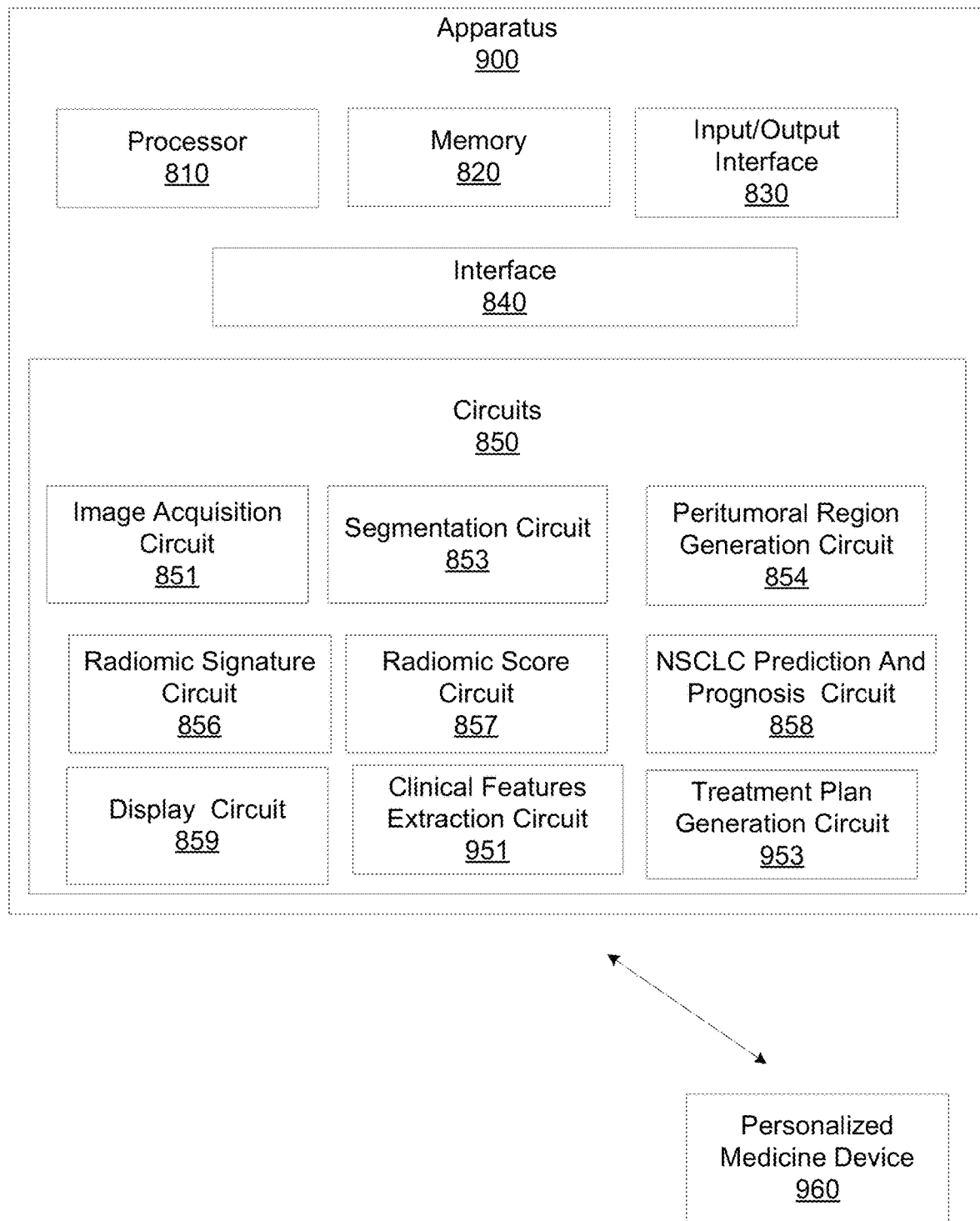
FIG. 9 illustrates an example apparatus for early stage NSCLC recurrence prognosis and added benefit of adjuvant chemotherapy prediction.

FIG. 9 illustrates an apparatus 900 that is similar to apparatus 800, but that includes additional elements and details. Apparatus 900 includes a clinical features extraction circuit 951. Clinical features extraction circuit 951 is configured to extract a set of clinical features from the radiological image. Extracting the set of clinical features includes acquiring electronic data, reading from a computer file, receiving a computer file, reading from a computer memory, or other computerized activity. In one embodiment, the set of clinical features includes at least one of a tumor size, a lymphovascular status, a T status, a Nodal status, or a pathologic stage. In another embodiment, the set of clinical features may include other, different clinical features.

In apparatus 900, NSCLC prediction and prognosis circuit 858 is further configured to compute the probability of added benefit of adjuvant chemotherapy based, at least in part, on the radiomic score and the set of clinical features. In this embodiment, NSCLC prediction and prognosis circuit 858 is further configured to generate the NSCLC recurrence prognosis based, at least in part, on the radiomic score and the set of clinical features. Embodiments are configured to compute the probability of added benefit, and the NSCLC recurrence prognosis, based on the radiomic score and the set of clinical features, with a concordance index of at least 0.70.

In embodiments described herein, NSCLC prediction and prognosis circuit 858 may be configured to compute the probability of added benefit or generate the NSCLC recurrence prognosis using a machine learning approach based on the radiomic signature. In one embodiment, NSCLC prediction and prognosis circuit 858 is configured as a machine learning classifier. In this embodiment, the machine learning classifier is trained on a set of training images. In one embodiment, the NSCLC prediction and prognosis circuit 858 is configured as an LDA machine learning classifier. In another embodiment, NSCLC prediction and prognosis circuit 858 may be configured as another type of machine learning or deep learning classifier, including as a QDA classifier, an RF classifier, or a CNN classifier. In another embodiment, NSCLC prediction and prognosis circuit 858 is configured to use other machine learning techniques, include deep learning techniques, to compute the probability of added benefit or generate the NSCLC recurrence prognosis. In one embodiment, NSCLC prediction and prognosis circuit 858 may be configured to compute the probability of added benefit or generate the NSCLC recurrence prognosis using a machine learning approach based on the radiomic signature and the set of clinical features.

Display circuit 859 may also control a CADx system, a monitor, or other display, to display operating parameters or characteristics of the set of circuits 850, including image acquisition circuit 851, segmentation circuit 853, peritumoral region generation circuit 854, radiomic signature circuit 856, radiomic score circuit 857, NSCLC prediction and prognosis circuit 858, and display circuit 859, including a machine learning classifier, during both training and testing, or during clinical operation of apparatus 800 or apparatus 900.

Apparatus 800 or apparatus 900 may further include a treatment plan generation circuit 953. The treatment plan generation circuit 953 may be configured to generate a personalized treatment plan based, at least in part, on the radiomic score, the NSCLC recurrence prognosis, or the probability of added benefit. In one embodiment, the personalized treatment plan is further based on the radiological image, or the radiomic signature. The personalized treatment plan may suggest a surgical treatment, may define an immunotherapy agent dosage or schedule, or a chemotherapy agent dosage or schedule, when the region of tissue has a higher radiomic score. For a region of tissue having a lower radiomic score, other treatments, schedules, or dosages may be suggested. In this embodiment, display circuit 859 may be configured to further display the personalized treatment plan.

In one embodiment, apparatus 800 or apparatus 900 may also include a training circuit. The training circuit may be configured to train radiomic signature circuit 856, radiomic score circuit 857, or NSCLC prediction and prognosis circuit 858 according to techniques described herein. Training radiomic signature circuit 856, radiomic score circuit 857, or NSCLC prediction and prognosis circuit 858 may include training a machine learning classifier, including a LDA classifier. In one embodiment, the training circuit is configured to access a training dataset of digitized images of a region of interest demonstrating early stage NSCLC. The training dataset includes radiological images of tissue that experience recurrence, and radiological images of tissue that did not experience recurrence. The training dataset may include radiological images of tissue that experienced recurrence at different times, for example, images of tissue with short-term DFS, and images of tissue with long-term DFS. The training circuit may be further configured to access a testing dataset of radiological images of a region of interest demonstrating early stage NSCLC, where the testing dataset includes radiological images of tissue that experience recurrence, and radiological images of tissue demonstrating NSCLC that did not experience recurrence. In this embodiment, the machine learning classifier is trained and tested using the training dataset of images and the testing dataset of images. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed.

FIG. 9 further illustrates a personalized medicine device 960. Apparatus 900 may be configured to transmit at least one of the radiomic score, the NSCLC recurrence prognosis, the probability of added benefit, the personalized treatment plan, or the radiological image to the personalized medicine device 960. Personalized medicine device 960 may be, for example, a CADx system, an early stage NSCLC recurrence prognosis system, an added benefit of adjuvant chemotherapy prediction system, or other type of personalized medicine device that may be used to facilitate the classification of tissue, recurrence prognosis, or the prediction of added benefit of chemotherapy. In one embodiment, apparatus 900 may control personalized medicine device 960 to display the radiomic score, the NSCLC recurrence prognosis, the probability of added benefit, the personalized treatment plan, the set of clinical features, or the radiological image on a computer monitor, a smartphone display, a tablet display, or other displays.

Figure 10:
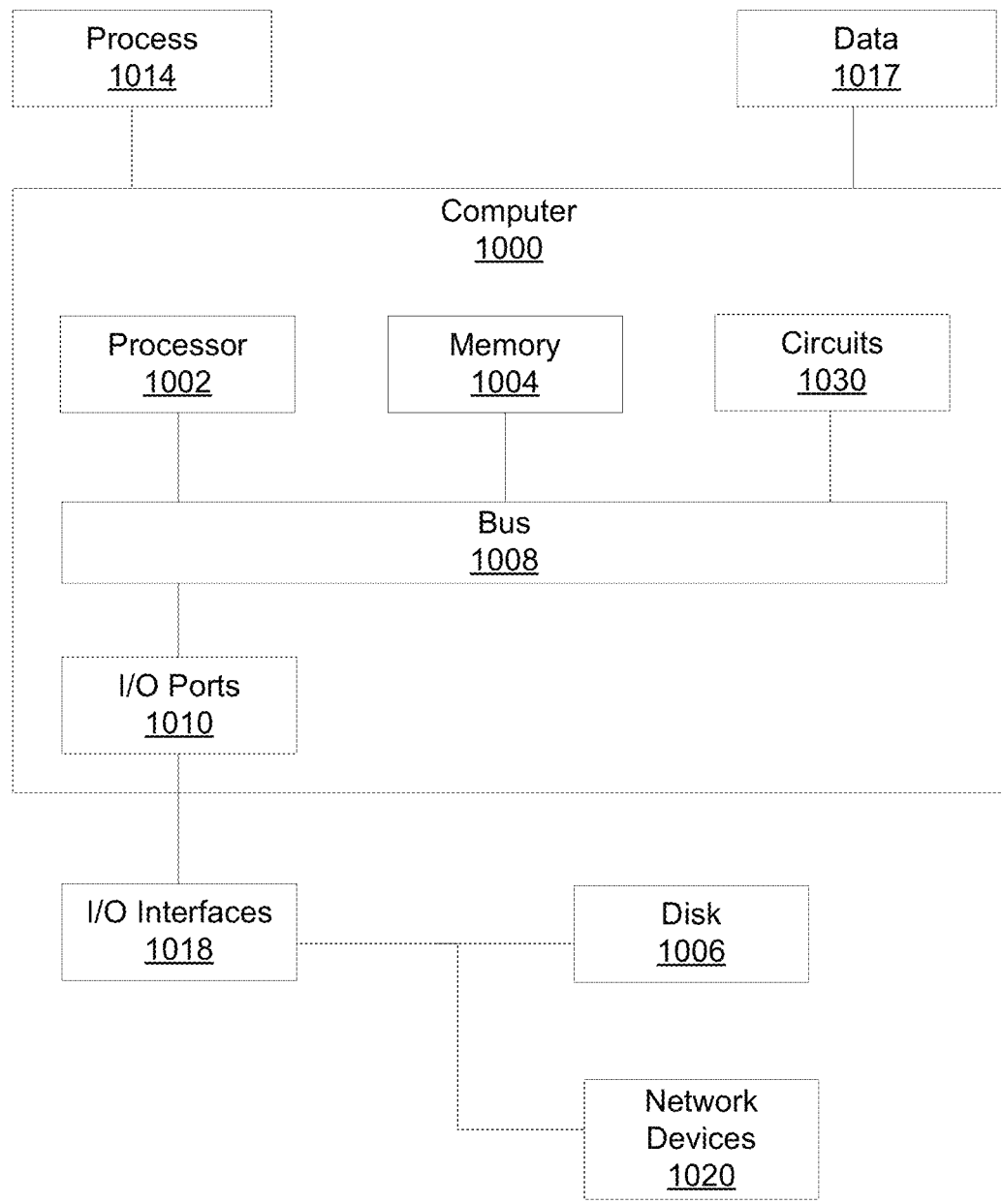
FIG. 10 illustrates an example computer in which embodiments described herein may operate.

FIG. 10 illustrates an example computer 1000 in which example methods illustrated herein can operate and in which example methods, apparatus, circuits, operations, or logics may be implemented. In different examples, computer 1000 may be part of a personalized medicine system, an early stage NSCLC recurrence prognosis system, an added benefit of adjuvant chemotherapy system, an MRI system, a digital whole slide scanner, a CT system, may be operably connectable to an early stage NSCLC recurrence prognosis system, an added benefit of adjuvant chemotherapy system, a CT system, an MRI system, a personalized medicine system, or a digital whole slide scanner, or may be part of a CADx system.

Computer 1000 includes a processor 1002, a memory 1004, and input/output (I/O) ports 1010 operably connected by a bus 1008. In one example, computer 1000 may include a set of logics or circuits 1030 that perform operations for or a method of early stage NSCLC recurrence prognosis, or of predicting added benefit of adjuvant chemotherapy, of regions of tissue demonstrating NSCLC in radiological images using a machine learning classifier. Thus, the set of circuits 1030, whether implemented in computer 1000 as hardware, firmware, software, and/or a combination thereof may provide means (e.g., hardware, firmware, circuits) for early stage NSCLC recurrence prognosis, or of predicting added benefit of adjuvant chemotherapy. In different examples, the set of circuits 1030 may be permanently and/or removably attached to computer 1000.

Processor 1002 can be a variety of various processors including dual microprocessor and other multi-processor architectures. Processor 1002 may be configured to perform operations or steps of methods claimed and described herein. Memory 1004 can include volatile memory and/or non-volatile memory. A disk 1006 may be operably connected to computer 1000 via, for example, an input/output interface (e.g., card, device) 1018 and an input/output port 1010. Disk 1006 may include, but is not limited to, devices like a magnetic disk drive, a tape drive, a Zip drive, a flash memory card, or a memory stick. Furthermore, disk 1006 may include optical drives like a CD-ROM or a digital video ROM drive (DVD ROM). Memory 1004 can store processes 1014 or data 1017, for example. Data 1017 may, in one embodiment, include digitized radiological images of tissue demonstrating early stage NSCLC. Disk 1006 or memory 1004 can store an operating system that controls and allocates resources of computer 1000.

Bus 1008 can be a single internal bus interconnect architecture or other bus or mesh architectures. While a single bus is illustrated, it is to be appreciated that computer 1000 may communicate with various devices, circuits, logics, and peripherals using other buses that are not illustrated (e.g., PCIE, SATA, Infiniband, 794, USB, Ethernet).

Computer 1000 may interact with input/output devices via I/O interfaces 1018 and input/output ports 1010. Input/output devices can include, but are not limited to, CT systems, MRI systems, digital whole slide scanners, an optical microscope, a keyboard, a microphone, a pointing and selection device, cameras, video cards, displays, disk 1006, network devices 1020, or other devices. Input/output ports 1010 can include but are not limited to, serial ports, parallel ports, or USB ports.

Computer 1000 may operate in a network environment and thus may be connected to network devices 1020 via I/O interfaces 1018 or I/O ports 1010. Through the network devices 1020, computer 1000 may interact with a network. Through the network, computer 1000 may be logically connected to remote computers. The networks with which computer 1000 may interact include, but are not limited to, a local area network (LAN), a wide area network (WAN), or other networks, including the cloud.

Figure 11:
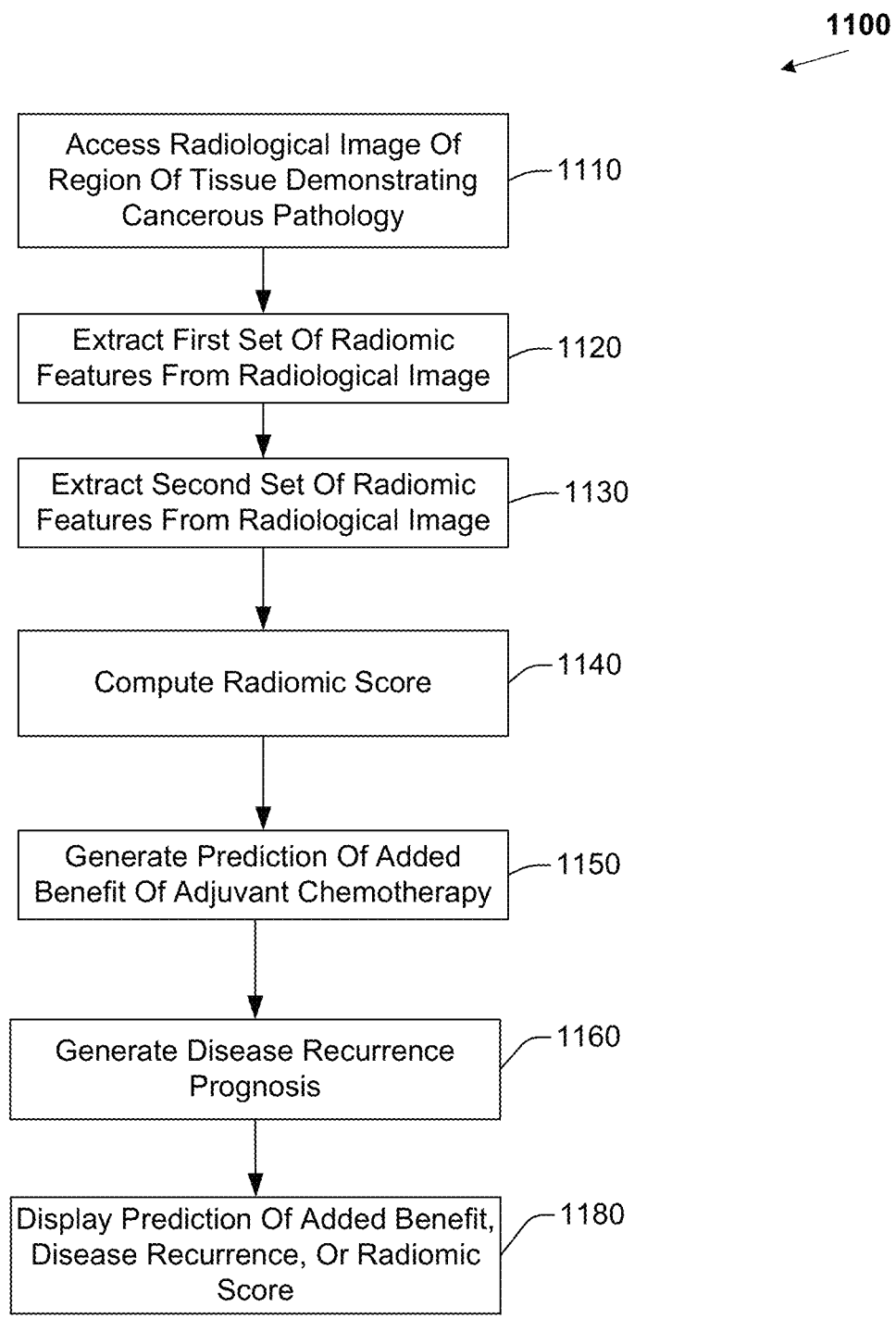
FIG. 11 illustrates an example method for early stage NSCLC recurrence prognosis and added benefit of adjuvant chemotherapy prediction.

FIG. 11 illustrates an example method 1100. Method 1100 includes, at 1110 accessing a radiological image of a region of tissue demonstrating early stage NSCLC. The radiological image has plurality of pixels. A pixel has an intensity. The region of tissue includes a tumor region. The radiological image includes a segmented tumor region and a peritumoral region. In one embodiment, the peritumoral region includes five annular rings, an annular ring having a dilation value of 3 mm. Accessing the radiological image includes acquiring electronic data, reading from a computer file, receiving a computer file, reading from a computer memory, or other computerized activity.

Method 1100 also includes, at 1120 extracting a first set of radiomic features from the segmented tumor region. Extracting the first set of radiomic features includes acquiring electronic data, reading from a computer file, receiving a computer file, reading from a computer memory, or other computerized activity.

Method 1100 also includes, at 1130, extracting a second, different set of radiomic features from the peritumoral region. The first set of radiomic features and the second, different set of radiomic features are selected based on a continuous disease free survival (DFS) time data. The first set of radiomic features, and the second, different set of radiomic features include at least one of a Haralick feature, a co-occurrence of local anisotropy gradients (CoLIAGe) feature, a Laws feature, a Laplace feature, or a Gabor feature. Extracting the second, different set of radiomic features includes acquiring electronic data, reading from a computer file, receiving a computer file, reading from a computer memory, or other computerized activity.

Method 1100 also includes, at 1140, computing a radiomic score. The radiomic score is computed based on a linear combination of a raw feature value of a member of the first set of radiomic features or a member of the second, different set of radiomic features, multiplied by a least absolute shrinkage and selection operator (LASSO) coefficient of the raw feature value of the member of the first set of radiomic features or the member of the second, different set of radiomic features, respectively.

Method 1100 also includes, at 1150, generating a prediction of added benefit of adjuvant chemotherapy. The prediction of added benefit is based, at least in part, on the radiomic score. Generating the prediction of added benefit includes acquiring electronic data, reading from a computer file, receiving a computer file, reading from a computer memory, or other computerized activity.

Method 1100 also includes, at 1160, generating a disease recurrence prognosis. The disease recurrence prognosis is based, at least in part, on the radiomic score. Generating the disease recurrence prognosis includes acquiring electronic data, reading from a computer file, receiving a computer file, reading from a computer memory, or other computerized activity.

Method 1100 also includes, at 1180, displaying at least one of the prediction of added benefit, the disease recurrence prognosis, or the radiomic score. Displaying at least one of the prediction of added benefit, the disease recurrence prognosis, or the radiomic score includes displaying at least one of the prediction of added benefit, the disease recurrence prognosis, or the radiomic score on a computer monitor, a smartphone display, a tablet display, or other displays.

Figure 12:
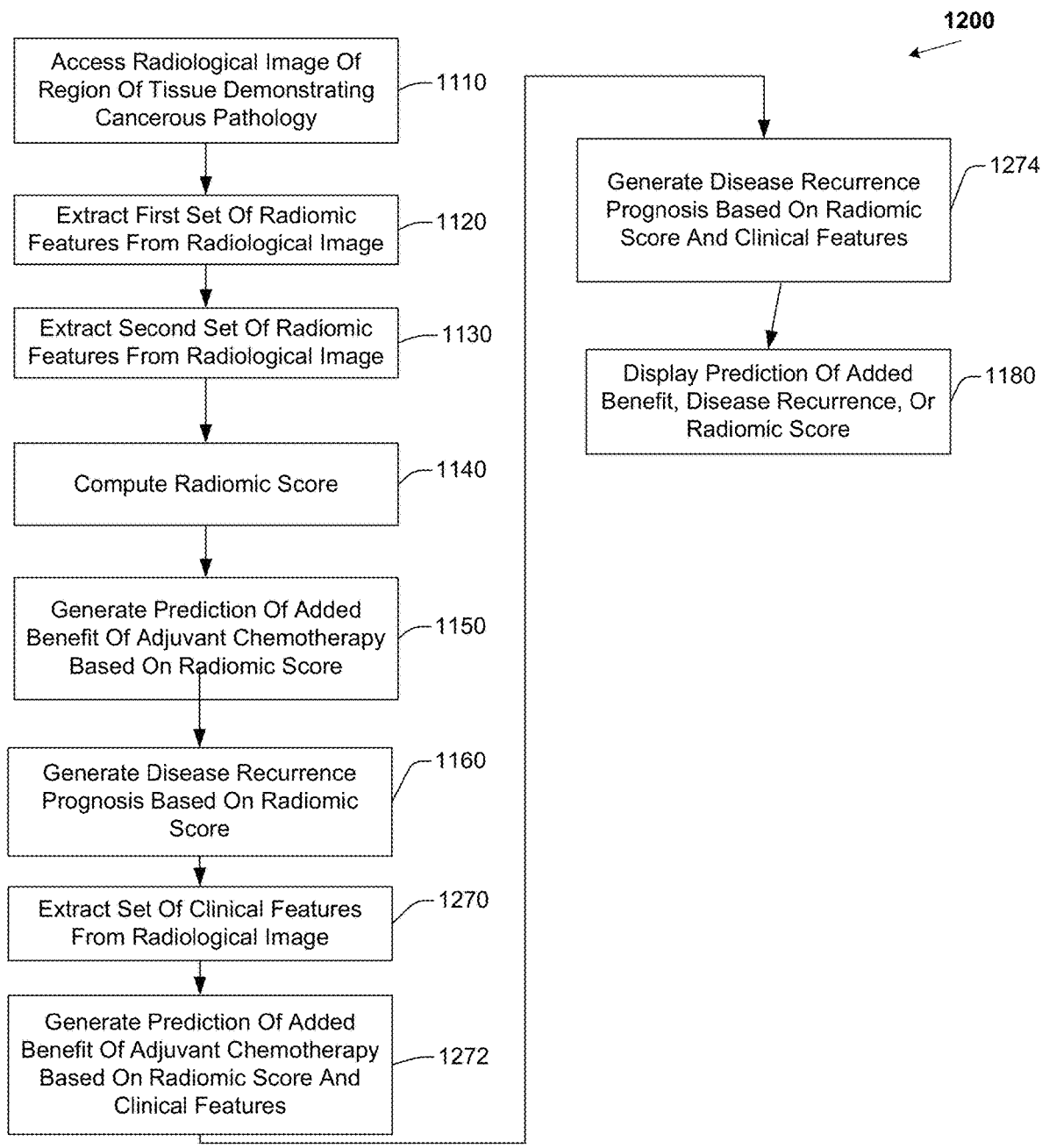
FIG. 12 illustrates an example method for early stage NSCLC recurrence prognosis and added benefit of adjuvant chemotherapy prediction.

FIG. 12 an example method 1200 that is similar to method 1100, but that includes additional steps and details. Method 1200 includes, at 1270, extracting a set of clinical features from the radiological image. The set of clinical features may include, in one embodiment, at least one of a tumor size, a lymphovascular status, a T status, a Nodal status, or a pathologic stage. In another embodiment, the set of clinical features may include other, different clinical features.

Method 1200 also includes, at 1272, generating the prediction of added benefit of adjuvant chemotherapy based, at least in part, on the radiomic score and the set of clinical features.

Method 1200 further includes, at 1274, generating the disease recurrence prognosis based, at least in part, on the radiomic score and the set of clinical features. In one embodiment, method 1200 may, at 1180, further display the set of clinical features.

Examples herein can include subject matter such as an apparatus, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for NSCLC recurrence prognosis, or for predicting added benefit of adjuvant chemotherapy, according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that when executed control a processor to perform operations, the operations comprising:

accessing a radiological image of a region of tissue demonstrating early stage non-small cell lung cancer (NSCLC), where the region of tissue includes a tumor;

defining a tumoral region by segmenting the tumor represented in the radiological image, where defining the tumoral region includes defining a tumoral boundary;

defining a peritumoral region based on a morphological dilation of the tumoral boundary;

extracting a radiomic signature from the radiological image, where the radiomic signature includes a set of tumoral radiomic features extracted from the tumoral region, and a set of peritumoral radiomic features extracted from the peritumoral region, where the set of tumoral radiomic features and the set of peritumoral radiomic features are selected based on a continuous time to event data;

computing a radiomic score based on the radiomic signature, where the radiomic score is computed using a linear combination of raw feature values weighted by coefficients, the raw feature values being of members of the set of tumoral radiomic features and the set of peritumoral radiomic features;

computing a probability of added benefit of adjuvant chemotherapy based, at least in part, on the radiomic score; and generating an NSCLC recurrence prognosis based, at least in part, on the radiomic score.

2. The non-transitory computer-readable storage device of claim 1, where the continuous time to event data is a disease free survival (DFS) time of a training set of radiological images of the region of tissue demonstrating early stage NSCLC.

3. The non-transitory computer-readable storage device of claim 1, where the radiomic score is computed using the linear combination of the raw feature values of the members of the set of tumoral radiomic features and the set of peritumoral radiomic features, multiplied by a least absolute shrinkage and selection operator (LASSO) coefficient of the raw feature values of the members of the set of tumoral radiomic features or the members of the set of peritumoral radiomic features, respectively.

4. The non-transitory computer-readable storage device of claim 1, where the peritumoral region includes a plurality of annular rings respectively having widths that collectively span the morphological dilation of the tumoral boundary.

5. The non-transitory computer-readable storage device of claim 4, where the morphological dilation of the tumoral boundary dilates the tumoral boundary by 15 mm.

6. The non-transitory computer-readable storage device of claim 5, where the peritumoral region includes five annular rings, a member of the five annular rings having a width of 3 mm.

7. The non-transitory computer-readable storage device of claim 1,
where the radiological image is a computed-tomography (CT) image having a plurality of slices,
where a member of the plurality of slices has a thickness of 1 mm to 5 mm.

8. The non-transitory computer-readable storage device of claim 1, where segmenting the tumor represented in the radiological image includes segmenting the tumor using watershed segmentation, region growing segmentation, or thresholding-based segmentation.

9. The non-transitory computer-readable storage device of claim 1,
where the NSCLC recurrence prognosis is inversely related to the radiomic score, and
where the probability of added benefit of adjuvant chemotherapy is directly related to the radiomic score.

10. The non-transitory computer-readable storage device of claim 1, the operations further comprising:
extracting a set of clinical features from the radiological image;
computing the probability of added benefit of adjuvant chemotherapy based, at least in part, on the radiomic score and the set of clinical features; and
generating the NSCLC recurrence prognosis based, at least in part, on the radiomic score and the set of clinical features.

11. The non-transitory computer-readable storage device of claim 10, where the set of clinical features includes at least one of a tumor size, a lymphovascular status, a T status, a Nodal status, or a pathologic stage.

12. The non-transitory computer-readable storage device of claim 10, the operations further comprising:
generating a personalized NSCLC treatment plan based on the radiomic score and at least one of the probability of added benefit of adjuvant chemotherapy, the NSCLC recurrence prognosis, or a member of the set of clinical features.

13. The non-transitory computer-readable storage device of claim 12, the operations further comprising displaying at least one of the radiomic score, the member of the set of clinical features, the probability of added benefit of adjuvant chemotherapy, the NSCLC recurrence prognosis, or the personalized NSCLC treatment plan.

14. The non-transitory computer-readable storage device of claim 1,
where the radiological image has a plurality of slices; and
where at least one slice of the plurality of slices has a thickness of 1 mm to 5 mm.

15. The non-transitory computer-readable storage device of claim 1, where the peritumoral region includes a plurality of annular rings, one of the plurality of annular rings having a width of 3 mm.

16. An apparatus for predicting recurrence in early stage non-small cell lung cancer (NSCLC), comprising:
a processor;
a memory configured to store a radiological image of a region of tissue demonstrating early stage NSCLC;
an input/output (I/O) interface;
a set of circuits; and
an interface that connects the processor, the memory, the I/O interface, and the set of circuits, the set of circuits comprising:
an image acquisition circuit configured to access the radiological image of the region of tissue demonstrating early stage NSCLC, where the region of tissue includes a tumor;
a segmentation circuit configured to define a tumoral region by segmenting the tumor represented in the radiological image, where defining the tumoral region includes defining a tumoral boundary;
a peritumoral region generation circuit configured to define a peritumoral region based on a morphological dilation of the tumoral boundary;
a radiomic signature circuit configured to extract a radiomic signature from the radiological image, where the radiomic signature includes a set of tumoral radiomic features extracted from the tumoral region, and a set of peritumoral radiomic features extracted from the peritumoral region, where the set of tumoral radiomic features and the set of peritumoral radiomic features are selected based on a continuous time to event data;
a radiomic score circuit configured to:
compute a radiomic score based on the radiomic signature;
an NSCLC prediction and prognosis circuit configured to:
compute a probability of added benefit of adjuvant chemotherapy based, at least in part, on the radiomic score; and
generate an NSCLC recurrence prognosis based, at least in part, on the radiomic score;
where the radiomic score circuit is configured to compute the radiomic score using a linear combination of a raw feature value of a member of the set of tumoral radiomic features or a member of the set of peritumoral radiomic features, multiplied by a coefficient of the raw feature value of the member of the set of tumoral radiomic features or the member of the set of peritumoral radiomic features, respectively; and
a display circuit configured to display the radiomic score, and at least one of the NSCLC recurrence prognosis, the probability of added benefit, or the radiological image.

17. The apparatus of claim 16, where the peritumoral region includes a plurality of annular rings spanning different parts of the morphological dilation of the tumoral boundary.

18. The apparatus of claim 16, where the radiomic score circuit is configured to compute the radiomic score using the linear combination of the raw feature value of the member of the set of tumoral radiomic features or the member of the set of peritumoral radiomic features, multiplied by a least absolute shrinkage and selection operator (LASSO) coefficient of the raw feature value of the member of the set of tumoral radiomic features or the member of the set of peritumoral radiomic features, respectively.

19. A non-transitory computer-readable storage device storing computer-executable instructions that when executed control a computer to perform a method, the method comprising:
- accessing a radiological image of a region of tissue demonstrating cancerous pathology, where the radiological image includes a segmented tumor region and a peritumoral region;
- extracting a first set of radiomic features from the segmented tumor region;
- extracting a second, different set of radiomic features from the peritumoral region, where the first set of radiomic features and the second, different set of radiomic features are selected based on a continuous disease free survival (DFS) time data;
- computing a radiomic score based on a linear combination of a raw feature value of a member of the first set of radiomic features or a member of the second, different set of radiomic features, multiplied by a least absolute shrinkage and selection operator (LASSO) coefficient of the raw feature value of the member of the first set of radiomic features or the member of the second, different set of radiomic features, respectively;
- generating a prediction of added benefit of adjuvant chemotherapy based, at least in part, on the radiomic score;
- generating a disease recurrence prognosis based, at least in part, on the radiomic score; and
- displaying at least one of the prediction of added benefit, the disease recurrence prognosis, or the radiomic score.

20. The non-transitory computer-readable storage device of claim 19, the method further comprising:
- extracting a set of clinical features from the radiological image;
- generating the prediction of added benefit of adjuvant chemotherapy based, at least in part, on the radiomic score and the set of clinical features; and
- generating the disease recurrence prognosis based, at least in part, on the radiomic score and the set of clinical features.

* * * * *